United States Patent
Inouye et al.

(10) Patent No.: US 9,957,487 B2
(45) Date of Patent: May 1, 2018

(54) **MUTATED GENES FOR THE CATALYTIC PROTEIN OF *OPLOPHORUS* LUCIFERASE AND USE THEREOF**

(71) Applicant: JNC CORPORATION, Tokyo (JP)

(72) Inventors: Satoshi Inouye, Kanagawa (JP); Junichi Sato, Kanagawa (JP)

(73) Assignee: JNC CORPORATION, Tokyo (JP)

( * ) Notice: Subject to any disclaimer, the term of this patent is extended or adjusted under 35 U.S.C. 154(b) by 33 days.

(21) Appl. No.: 14/516,666

(22) Filed: Oct. 17, 2014

(65) Prior Publication Data
US 2015/0111233 A1  Apr. 23, 2015

(30) Foreign Application Priority Data
Oct. 21, 2013 (JP) ................. 2013-218111

(51) Int. Cl.
C12N 9/02 (2006.01)
C12Q 1/66 (2006.01)
C07K 14/435 (2006.01)

(52) U.S. Cl.
CPC ...... *C12N 9/0069* (2013.01); *C07K 14/43509* (2013.01); *C12Q 1/66* (2013.01); *C12Y 113/12007* (2013.01)

(58) Field of Classification Search
None
See application file for complete search history.

(56) References Cited

U.S. PATENT DOCUMENTS

| | | | |
|---|---|---|---|
| 7,723,502 B2 | 5/2010 | Coleman et al. | |
| 2002/0102687 A1 | 8/2002 | Inouye | |
| 2010/0281552 A1* | 11/2010 | Encell | C12Q 1/66 800/13 |
| 2012/0117667 A1 | 5/2012 | Klaubert et al. | |
| 2012/0174242 A1* | 7/2012 | Binkowski | C07D 487/04 800/13 |
| 2014/0223590 A1 | 8/2014 | Binkowski et al. | |

FOREIGN PATENT DOCUMENTS

| | | |
|---|---|---|
| GB | 2425535 A | 11/2006 |
| GB | 2479847 A | 10/2011 |
| JP | 2002-320482 A | 11/2002 |
| JP | 2008-000073 A | 1/2008 |
| JP | 4613441 B2 | 1/2011 |
| JP | 2012-525819 A | 10/2012 |
| WO | WO-03040100 A1 | 5/2003 |
| WO | WO-2004042010 A2 | 5/2004 |
| WO | WO-2010/127368 A1 | 11/2010 |
| WO | WO-2011007314 A1 | 1/2011 |
| WO | WO-2011025980 A1 | 3/2011 |
| WO | WO-2012061529 A1 | 5/2012 |
| WO | WO-2012061530 A2 | 5/2012 |
| WO | WO-2012061530 A3 | 9/2012 |
| WO | WO-2012061530 A8 | 6/2013 |

OTHER PUBLICATIONS

Ngo et al. In The Protein Folding Problem and Tertiary Structure Prediction, 1994, Merz et al. (ed.), Birkhauser, Boston, MA, pp. 433 and 492-495.*
GB Application No. 1422600.5—Search Report dated Sep. 15, 2015.
Inouye, et al., "Unconventional secretion of the mutated 159 kDa protein of *Oplophorus* luciferase (nanoKAZ) in mammalian cells", Biochemical and Biophysical Research Communications, Jul. 11, 2014, vol. 450, , No. 4, pp. 1313-1319.
GB Application No. 1406130.3—Search Report dated Nov. 11, 2014.
GB Application No. 1403374.0—Search Report dated Nov. 12, 2014.
Inouye, et al., "Soluble protein expression in *E. coli* cells using IgG-binding domain of protein A as a solubilizing partner in the cold induced system", Biochem. Biophys. Res. Commun., 2008, 376, pp. 448-453.
Inouye, et al., "The Use of *Renilla* Luciferase, *Oplophorus* Luciferase, and Apoaequorin as Bioluminescent Reporter Protein in the Presence of Coelenterazine Analogues as Substrate", Biochem. Biophys. Res. Commun., 1997, 223, pp. 349-353.
Nakamura, et al., "Efficient Bioluminescence of Bisdeoxycoelenterazine with the Luciferase of a Deep-Sea Shrimp *Oplophorus*", Tetrahedron Lett., 1997, vol. 38, No. 6, pp. 6405-6406.
Wu, et al., "Chemi- and bioluminescence of coelenterazine analogues with a conjugated group at the C-8 position", Tetrahedron Lett., 2001, 42, pp. 2997-3000.
Shimomura, et al., "Recombinant aequorin and recombinant semi-synthetic aequorins," Biochem. J., 1990, vol. 270, pp. 309-312.
Shimomura, et al., "Semi-sysnthetic aequorin, An improved tool for the measurement of calcium ion concentration," Biochem. J., 1988, vol. 251, pp. 405-410.
Shimomura, et al., "Semi-synthetic aequorins with improved sensitivity to $Ca^{2+}$ ions," Biochem. J., 1989, vol. 261, pp. 913-920.
Katsuhori Teranishi, "Luminescence of imidazo[1,2-a]pyrazin-3(7H)-one compounds," Bioorganic Chemistry, 2007, 25, pp. 82-111.
GB1418471.7—Search Report dated Jun. 25. 2015.
Osamu Shimomura, et al., "Properties and Reaction Mechanism of the Bioluminescence System of the Deep-Sea Shrimp *Oplophorus gracilorostris*," Biochemistry 17 (1978),pp. 994-998.
Satoshi Inouye, et al., "Secretional luciferase of the luminous shrimp *Oplophorus gracilirostris*: cDNA cloning of a novel imidazopyrazinone luciferase[1]," FEBS Letters 481 (2000), pp. 19-25.
Satoshi Inouye, et al., "Overexpression, purification and characterization of the catalytic component of *Oplophorus* luciferase in the deep-sea shrimp, *Oplophorus gracilirostris*," Protein Expression and Purification 56 (2007), pp. 261-268.
Mary P. Hall, et al., "Engineered Luciferase Reporter from a Deep Sea Shrimp Utilizing a Novel Imidazopyrazinone Substrate," ACS Chem. Biol. 7, 2012, pp. 1848-1857.

(Continued)

Primary Examiner — Richard G Hutson
(74) Attorney, Agent, or Firm — Drinker Biddle & Reath LLP

(57) ABSTRACT

Luciferases which are different from those known heretofore have been desired. A luciferase mutant comprising an amino acid sequence in which at least one amino acid selected from the group consisting of valine at the position of 44, alanine at the position of 54 and tyrosine at the position of 138 is substituted with other amino acid(s) in the amino acid sequence of SEQ ID NO: 2.

8 Claims, 4 Drawing Sheets
(4 of 4 Drawing Sheet(s) Filed in Color)

(56) References Cited

OTHER PUBLICATIONS

Satoshi Inouye, et al., "C6-Deoxy coelenterazine analogues as an efficient substrate for glow luminescence reaction of nanoKAZ: The mutated catalytic 19 kDa component of *Oplophorus* luciferase," Biochemical and Biophysical Research Communications 437 (2013), pp. 23-28.
Satoshi Inouye, et al., "Expression, purification and luminescence properties of coelenterazine-utilizing luciferases form *Renilla, Oplophorus* and *Gaussia*: Comparison of substrate specificity for C2-modified coelenterazines," Protein Expression and Purification 88 (2013) pp. 150-156.
JP 2013-080734—Office Action dated Jun. 28, 2016.
JP Application 2016-001665—Notice of Reasons for Refusal dated Oct. 16, 2016 (including English translation).
Pichler, et al., "Imaging reversal of multidrug resistance in living mice with bioluminescence: MDR1 P-glycoprotein transports coelenterazine", Proc. Natl. Acad. Sci., 2004, vol. 101, No. 6, pp. 1702-1707.
Inouye, et al., "Codon optimization of genes for efficient protein expression in mammalian cells by selection of only preferred human codons", Protein Expr. Purif., 2015, 109, pp. 47-54.

\* cited by examiner

Supernatant

Precipitate

Supernatant

Precipitate

SEQUENCE LISTING

```
<160> NUMBER OF SEQ ID NOS: 53

<210> SEQ ID NO 1
<211> LENGTH: 510
<212> TYPE: DNA
<213> ORGANISM: Oplophorus gracilirostris
<220> FEATURE:
<221> NAME/KEY: CDS
<222> LOCATION: (1)..(510)

<400> SEQUENCE: 1 ttt acg ttg gca gat ttc gtt gga gac tgg caa cag aca gct gga tac      48
Phe Thr Leu Ala Asp Phe Val Gly Asp Trp Gln Gln Thr Ala Gly Tyr
1               5                   10                  15 aac caa gat caa gtg tta gaa caa gga gga ttg tct agt ctg ttc caa      96
Asn Gln Asp Gln Val Leu Glu Gln Gly Gly Leu Ser Ser Leu Phe Gln
            20                  25                  30 gcc ctg gga gtg tca gtc acg ccc ata cag aaa gtt gta ctg tct ggg     144
Ala Leu Gly Val Ser Val Thr Pro Ile Gln Lys Val Val Leu Ser Gly
        35                  40                  45 gag aat ggg tta aaa gct gat att cat gtc ata ata cct tac gag gga     192
Glu Asn Gly Leu Lys Ala Asp Ile His Val Ile Ile Pro Tyr Glu Gly
    50                  55                  60 ctc agt ggt ttt caa atg ggt cta att gaa atg atc ttc aaa gtt gtt     240
Leu Ser Gly Phe Gln Met Gly Leu Ile Glu Met Ile Phe Lys Val Val
65                  70                  75                  80 tac ccc gtg gat gat cat cat ttc aag att att ctc cat tat ggt aca     288
Tyr Pro Val Asp Asp His His Phe Lys Ile Ile Leu His Tyr Gly Thr
                85                  90                  95 ctc gtt att gac ggt gta aca ccc aac atg att gac tac ttt gga aga     336
Leu Val Ile Asp Gly Val Thr Pro Asn Met Ile Asp Tyr Phe Gly Arg
            100                 105                 110 cct tac cct gga att gct gta ttt gac ggc aag cag atc aca gtt act     384
Pro Tyr Pro Gly Ile Ala Val Phe Asp Gly Lys Gln Ile Thr Val Thr
        115                 120                 125 gga act ctg tgg aac ggc aac aag atc tat gat gag agg cta atc aac     432
Gly Thr Leu Trp Asn Gly Asn Lys Ile Tyr Asp Glu Arg Leu Ile Asn
    130                 135                 140 cct gat ggt tca ctc ctc ttc aga gtt act atc aat gga gtc acg gga     480
Pro Asp Gly Ser Leu Leu Phe Arg Val Thr Ile Asn Gly Val Thr Gly
145                 150                 155                 160 tgg agg ctt tgc gag aac att ctt gcc taa                             510
Trp Arg Leu Cys Glu Asn Ile Leu Ala
                165
```

<210> SEQ ID NO 2
<211> LENGTH: 169
<212> TYPE: PRT
<213> ORGANISM: Oplophorus gracilirostris

<400> SEQUENCE: 2

```
Phe Thr Leu Ala Asp Phe Val Gly Asp Trp Gln Gln Thr Ala Gly Tyr
1               5                   10                  15

Asn Gln Asp Gln Val Leu Glu Gln Gly Gly Leu Ser Ser Leu Phe Gln
            20                  25                  30

Ala Leu Gly Val Ser Val Thr Pro Ile Gln Lys Val Val Leu Ser Gly
        35                  40                  45

Glu Asn Gly Leu Lys Ala Asp Ile His Val Ile Ile Pro Tyr Glu Gly
50                  55                  60

Leu Ser Gly Phe Gln Met Gly Leu Ile Glu Met Ile Phe Lys Val Val
65                  70                  75                  80

Tyr Pro Val Asp Asp His His Phe Lys Ile Ile Leu His Tyr Gly Thr
                85                  90                  95

Leu Val Ile Asp Gly Val Thr Pro Asn Met Ile Asp Tyr Phe Gly Arg
            100                 105                 110

Pro Tyr Pro Gly Ile Ala Val Phe Asp Gly Lys Gln Ile Thr Val Thr
        115                 120                 125

Gly Thr Leu Trp Asn Gly Asn Lys Ile Tyr Asp Glu Arg Leu Ile Asn
130                 135                 140

Pro Asp Gly Ser Leu Leu Phe Arg Val Thr Ile Asn Gly Val Thr Gly
145                 150                 155                 160

Trp Arg Leu Cys Glu Asn Ile Leu Ala
                165
```

<210> SEQ ID NO 3
<211> LENGTH: 510
<212> TYPE: DNA
<213> ORGANISM: Artificial sequence
<220> FEATURE:
<223> OTHER INFORMATION: synthetic DNA
<220> FEATURE:
<221> NAME/KEY: CDS
<222> LOCATION: (1)..(510)

<400> SEQUENCE: 3

```
ttt acg ttg gca gat ttc gtt gga gac tgg caa cag aca gct gga tac      48
Phe Thr Leu Ala Asp Phe Val Gly Asp Trp Gln Gln Thr Ala Gly Tyr
1               5                   10                  15 aac caa gat caa gtg tta gaa caa gga gga ttg tct agt ctg ttc caa      96
Asn Gln Asp Gln Val Leu Glu Gln Gly Gly Leu Ser Ser Leu Phe Gln
            20                  25                  30 gcc ctg gga gtg tca gtc acg ccc ata cag aaa atc gta ctg tct ggg     144
Ala Leu Gly Val Ser Val Thr Pro Ile Gln Lys Ile Val Leu Ser Gly
        35                  40                  45 gag aat ggg tta aaa gct gat att cat gtc ata ata cct tac gag gga     192
Glu Asn Gly Leu Lys Ala Asp Ile His Val Ile Ile Pro Tyr Glu Gly
50                  55                  60 ctc agt ggt ttt caa atg ggt cta att gaa atg atc ttc aaa gtt gtt     240
Leu Ser Gly Phe Gln Met Gly Leu Ile Glu Met Ile Phe Lys Val Val
65                  70                  75                  80 tac ccc gtg gat gat cat cat ttc aag att att ctc cat tat ggt aca     288
Tyr Pro Val Asp Asp His His Phe Lys Ile Ile Leu His Tyr Gly Thr
                85                  90                  95
```

```
ctc gtt att gac ggt gta aca ccc aac atg att gac tac ttt gga aga      336
Leu Val Ile Asp Gly Val Thr Pro Asn Met Ile Asp Tyr Phe Gly Arg
            100                 105                 110 cct tac cct gga att gct gta ttt gac ggc aag cag atc aca gtt act      384
Pro Tyr Pro Gly Ile Ala Val Phe Asp Gly Lys Gln Ile Thr Val Thr
        115                 120                 125 gga act ctg tgg aac ggc aac aag atc tat gat gag agg cta atc aac      432
Gly Thr Leu Trp Asn Gly Asn Lys Ile Tyr Asp Glu Arg Leu Ile Asn
    130                 135                 140 cct gat ggt tca ctc ctc ttc aga gtt act atc aat gga gtc acg gga      480
Pro Asp Gly Ser Leu Leu Phe Arg Val Thr Ile Asn Gly Val Thr Gly
145                 150                 155                 160 tgg agg ctt tgc gag aac att ctt gcc taa                              510
Trp Arg Leu Cys Glu Asn Ile Leu Ala
                165
```

<210> SEQ ID NO 4
<211> LENGTH: 169
<212> TYPE: PRT
<213> ORGANISM: Artificial sequence
<220> FEATURE:
<223> OTHER INFORMATION: Synthetic Construct

<400> SEQUENCE: 4

```
Phe Thr Leu Ala Asp Phe Val Gly Asp Trp Gln Gln Thr Ala Gly Tyr
1               5                   10                  15

Asn Gln Asp Gln Val Leu Glu Gln Gly Gly Leu Ser Ser Leu Phe Gln
            20                  25                  30

Ala Leu Gly Val Ser Val Thr Pro Ile Gln Lys Ile Val Leu Ser Gly
        35                  40                  45

Glu Asn Gly Leu Lys Ala Asp Ile His Val Ile Ile Pro Tyr Glu Gly
    50                  55                  60

Leu Ser Gly Phe Gln Met Gly Leu Ile Glu Met Ile Phe Lys Val Val
65                  70                  75                  80

Tyr Pro Val Asp Asp His His Phe Lys Ile Ile Leu His Tyr Gly Thr
                85                  90                  95

Leu Val Ile Asp Gly Val Thr Pro Asn Met Ile Asp Tyr Phe Gly Arg
            100                 105                 110

Pro Tyr Pro Gly Ile Ala Val Phe Asp Gly Lys Gln Ile Thr Val Thr
        115                 120                 125

Gly Thr Leu Trp Asn Gly Asn Lys Ile Tyr Asp Glu Arg Leu Ile Asn
    130                 135                 140

Pro Asp Gly Ser Leu Leu Phe Arg Val Thr Ile Asn Gly Val Thr Gly
145                 150                 155                 160

Trp Arg Leu Cys Glu Asn Ile Leu Ala
                165
```

<210> SEQ ID NO 5
<211> LENGTH: 510
<212> TYPE: DNA
<213> ORGANISM: Artificial sequence
<220> FEATURE:
<223> OTHER INFORMATION: synthetic DNA
<220> FEATURE:
<221> NAME/KEY: CDS
<222> LOCATION: (1)..(510)

<400> SEQUENCE: 5

```
ttt acg ttg gca gat ttc gtt gga gac tgg caa cag aca gct gga tac      48
Phe Thr Leu Ala Asp Phe Val Gly Asp Trp Gln Gln Thr Ala Gly Tyr
1               5                   10                  15
```

```
aac caa gat caa gtg tta gaa caa gga gga ttg tct agt ctg ttc caa      96
Asn Gln Asp Gln Val Leu Glu Gln Gly Gly Leu Ser Ser Leu Phe Gln
            20                  25                  30 gcc ctg gga gtg tca gtc acg ccc ata cag aaa gtt gta ctg tct ggg     144
Ala Leu Gly Val Ser Val Thr Pro Ile Gln Lys Val Val Leu Ser Gly
        35                  40                  45 gag aat ggg tta aaa atc gat att cat gtc ata ata cct tac gag gga     192
Glu Asn Gly Leu Lys Ile Asp Ile His Val Ile Ile Pro Tyr Glu Gly
    50                  55                  60 ctc agt ggt ttt caa atg ggt cta att gaa atg atc ttc aaa gtt gtt     240
Leu Ser Gly Phe Gln Met Gly Leu Ile Glu Met Ile Phe Lys Val Val
65                  70                  75                  80 tac ccc gtg gat gat cat cat ttc aag att att ctc cat tat ggt aca     288
Tyr Pro Val Asp Asp His His Phe Lys Ile Ile Leu His Tyr Gly Thr
                85                  90                  95 ctc gtt att gac ggt gta aca ccc aac atg att gac tac ttt gga aga     336
Leu Val Ile Asp Gly Val Thr Pro Asn Met Ile Asp Tyr Phe Gly Arg
            100                 105                 110 cct tac cct gga att gct gta ttt gac ggc aag cag atc aca gtt act     384
Pro Tyr Pro Gly Ile Ala Val Phe Asp Gly Lys Gln Ile Thr Val Thr
        115                 120                 125 gga act ctg tgg aac ggc aac aag atc tat gat gag agg cta atc aac     432
Gly Thr Leu Trp Asn Gly Asn Lys Ile Tyr Asp Glu Arg Leu Ile Asn
    130                 135                 140 cct gat ggt tca ctc ctc ttc aga gtt act atc aat gga gtc acg gga     480
Pro Asp Gly Ser Leu Leu Phe Arg Val Thr Ile Asn Gly Val Thr Gly
145                 150                 155                 160 tgg agg ctt tgc gag aac att ctt gcc taa                             510
Trp Arg Leu Cys Glu Asn Ile Leu Ala
                165
```

<210> SEQ ID NO 6
<211> LENGTH: 169
<212> TYPE: PRT
<213> ORGANISM: Artificial sequence
<220> FEATURE:
<223> OTHER INFORMATION: Synthetic Construct

<400> SEQUENCE: 6

```
Phe Thr Leu Ala Asp Phe Val Gly Asp Trp Gln Gln Thr Ala Gly Tyr
1               5                   10                  15

Asn Gln Asp Gln Val Leu Glu Gln Gly Gly Leu Ser Ser Leu Phe Gln
            20                  25                  30

Ala Leu Gly Val Ser Val Thr Pro Ile Gln Lys Val Val Leu Ser Gly
        35                  40                  45

Glu Asn Gly Leu Lys Ile Asp Ile His Val Ile Ile Pro Tyr Glu Gly
    50                  55                  60

Leu Ser Gly Phe Gln Met Gly Leu Ile Glu Met Ile Phe Lys Val Val
65                  70                  75                  80

Tyr Pro Val Asp Asp His His Phe Lys Ile Ile Leu His Tyr Gly Thr
                85                  90                  95

Leu Val Ile Asp Gly Val Thr Pro Asn Met Ile Asp Tyr Phe Gly Arg
            100                 105                 110

Pro Tyr Pro Gly Ile Ala Val Phe Asp Gly Lys Gln Ile Thr Val Thr
        115                 120                 125

Gly Thr Leu Trp Asn Gly Asn Lys Ile Tyr Asp Glu Arg Leu Ile Asn
    130                 135                 140

Pro Asp Gly Ser Leu Leu Phe Arg Val Thr Ile Asn Gly Val Thr Gly
```

Trp Arg Leu Cys Glu Asn Ile Leu Ala
                165

<210> SEQ ID NO 7
<211> LENGTH: 510
<212> TYPE: DNA
<213> ORGANISM: Artificial sequence
<220> FEATURE:
<223> OTHER INFORMATION: synthetic DNA
<220> FEATURE:
<221> NAME/KEY: CDS
<222> LOCATION: (1)..(510)

<400> SEQUENCE: 7

| ttt acg ttg gca gat ttc gtt gga gac tgg caa cag aca gct gga tac | 48 |
|---|---|
| Phe Thr Leu Ala Asp Phe Val Gly Asp Trp Gln Gln Thr Ala Gly Tyr | |
| 1               5                  10                  15 | |
| aac caa gat caa gtg tta gaa caa gga gga ttg tct agt ctg ttc caa | 96 |
| Asn Gln Asp Gln Val Leu Glu Gln Gly Gly Leu Ser Ser Leu Phe Gln | |
|            20                  25                  30 | |
| gcc ctg gga gtg tca gtc acg ccc ata cag aaa gtt gta ctg tct ggg | 144 |
| Ala Leu Gly Val Ser Val Thr Pro Ile Gln Lys Val Val Leu Ser Gly | |
|        35                  40                  45 | |
| gag aat ggg tta aaa gct gat att cat gtc ata ata cct tac gag gga | 192 |
| Glu Asn Gly Leu Lys Ala Asp Ile His Val Ile Ile Pro Tyr Glu Gly | |
|    50                  55                  60 | |
| ctc agt ggt ttt caa atg ggt cta att gaa atg atc ttc aaa gtt gtt | 240 |
| Leu Ser Gly Phe Gln Met Gly Leu Ile Glu Met Ile Phe Lys Val Val | |
| 65                  70                  75                  80 | |
| tac ccc gtg gat gat cat cat ttc aag att att ctc cat tat ggt aca | 288 |
| Tyr Pro Val Asp Asp His His Phe Lys Ile Ile Leu His Tyr Gly Thr | |
|                85                  90                  95 | |
| ctc gtt att gac ggt gta aca ccc aac atg att gac tac ttt gga aga | 336 |
| Leu Val Ile Asp Gly Val Thr Pro Asn Met Ile Asp Tyr Phe Gly Arg | |
|            100                 105                 110 | |
| cct tac cct gga att gct gta ttt gac ggc aag cag atc aca gtt act | 384 |
| Pro Tyr Pro Gly Ile Ala Val Phe Asp Gly Lys Gln Ile Thr Val Thr | |
|        115                 120                 125 | |
| gga act ctg tgg aac ggc aac aag atc atc gat gag agg cta atc aac | 432 |
| Gly Thr Leu Trp Asn Gly Asn Lys Ile Ile Asp Glu Arg Leu Ile Asn | |
|    130                 135                 140 | |
| cct gat ggt tca ctc ctc ttc aga gtt act atc aat gga gtc acg gga | 480 |
| Pro Asp Gly Ser Leu Leu Phe Arg Val Thr Ile Asn Gly Val Thr Gly | |
| 145                 150                 155                 160 | |
| tgg agg ctt tgc gag aac att ctt gcc taa | 510 |
| Trp Arg Leu Cys Glu Asn Ile Leu Ala | |
|                165 | |

<210> SEQ ID NO 8
<211> LENGTH: 169
<212> TYPE: PRT
<213> ORGANISM: Artificial sequence
<220> FEATURE:
<223> OTHER INFORMATION: Synthetic Construct

<400> SEQUENCE: 8

Phe Thr Leu Ala Asp Phe Val Gly Asp Trp Gln Gln Thr Ala Gly Tyr
1               5                  10                  15

Asn Gln Asp Gln Val Leu Glu Gln Gly Gly Leu Ser Ser Leu Phe Gln
            20                  25                  30

Ala Leu Gly Val Ser Val Thr Pro Ile Gln Lys Val Val Leu Ser Gly

```
                    35                  40                  45
Glu Asn Gly Leu Lys Ala Asp Ile His Val Ile Ile Pro Tyr Glu Gly
        50                  55                  60
Leu Ser Gly Phe Gln Met Gly Leu Ile Glu Met Ile Phe Lys Val Val
65                  70                  75                  80
Tyr Pro Val Asp Asp His His Phe Lys Ile Ile Leu His Tyr Gly Thr
                85                  90                  95
Leu Val Ile Asp Gly Val Thr Pro Asn Met Ile Asp Tyr Phe Gly Arg
            100                 105                 110
Pro Tyr Pro Gly Ile Ala Val Phe Asp Gly Lys Gln Ile Thr Val Thr
        115                 120                 125
Gly Thr Leu Trp Asn Gly Asn Lys Ile Ile Asp Glu Arg Leu Ile Asn
    130                 135                 140
Pro Asp Gly Ser Leu Leu Phe Arg Val Thr Ile Asn Gly Val Thr Gly
145                 150                 155                 160
Trp Arg Leu Cys Glu Asn Ile Leu Ala
                165
```

<210> SEQ ID NO 9
<211> LENGTH: 510
<212> TYPE: DNA
<213> ORGANISM: Artificial sequence
<220> FEATURE:
<223> OTHER INFORMATION: synthetic DNA
<220> FEATURE:
<221> NAME/KEY: CDS
<222> LOCATION: (1)..(510)

<400> SEQUENCE: 9

```
ttt acg ttg gca gat ttc gtt gga gac tgg caa cag aca gct gga tac      48
Phe Thr Leu Ala Asp Phe Val Gly Asp Trp Gln Gln Thr Ala Gly Tyr
1               5                  10                  15 aac caa gat caa gtg tta gaa caa gga gga ttg tct agt ctg ttc caa      96
Asn Gln Asp Gln Val Leu Glu Gln Gly Gly Leu Ser Ser Leu Phe Gln
                20                  25                  30 gcc ctg gga gtg tca gtc acg ccc ata cag aaa atc gta ctg tct ggg     144
Ala Leu Gly Val Ser Val Thr Pro Ile Gln Lys Ile Val Leu Ser Gly
            35                  40                  45 gag aat ggg tta aaa atc gat att cat gtc ata ata cct tac gag gga     192
Glu Asn Gly Leu Lys Ile Asp Ile His Val Ile Ile Pro Tyr Glu Gly
        50                  55                  60 ctc agt ggt ttt caa atg ggt cta att gaa atg atc ttc aaa gtt gtt     240
Leu Ser Gly Phe Gln Met Gly Leu Ile Glu Met Ile Phe Lys Val Val
65                  70                  75                  80 tac ccc gtg gat gat cat cat ttc aag att att ctc cat tat ggt aca     288
Tyr Pro Val Asp Asp His His Phe Lys Ile Ile Leu His Tyr Gly Thr
                85                  90                  95 ctc gtt att gac ggt gta aca ccc aac atg att gac tac ttt gga aga     336
Leu Val Ile Asp Gly Val Thr Pro Asn Met Ile Asp Tyr Phe Gly Arg
            100                 105                 110 cct tac cct gga att gct gta ttt gac ggc aag cag atc aca gtt act     384
Pro Tyr Pro Gly Ile Ala Val Phe Asp Gly Lys Gln Ile Thr Val Thr
        115                 120                 125 gga act ctg tgg aac ggc aac aag atc tat gat gag agg cta atc aac     432
Gly Thr Leu Trp Asn Gly Asn Lys Ile Tyr Asp Glu Arg Leu Ile Asn
    130                 135                 140 cct gat ggt tca ctc ctc ttc aga gtt act atc aat gga gtc acg gga     480
Pro Asp Gly Ser Leu Leu Phe Arg Val Thr Ile Asn Gly Val Thr Gly
145                 150                 155                 160
```

```
tgg agg ctt tgc gag aac att ctt gcc taa                            510
Trp Arg Leu Cys Glu Asn Ile Leu Ala
                165

<210> SEQ ID NO 10
<211> LENGTH: 169
<212> TYPE: PRT
<213> ORGANISM: Artificial sequence
<220> FEATURE:
<223> OTHER INFORMATION: Synthetic Construct

<400> SEQUENCE: 10

Phe Thr Leu Ala Asp Phe Val Gly Asp Trp Gln Gln Thr Ala Gly Tyr
1               5                   10                  15

Asn Gln Asp Gln Val Leu Glu Gln Gly Gly Leu Ser Ser Leu Phe Gln
            20                  25                  30

Ala Leu Gly Val Ser Val Thr Pro Ile Gln Lys Ile Val Leu Ser Gly
        35                  40                  45

Glu Asn Gly Leu Lys Ile Asp Ile His Val Ile Ile Pro Tyr Glu Gly
    50                  55                  60

Leu Ser Gly Phe Gln Met Gly Leu Ile Glu Met Ile Phe Lys Val Val
65                  70                  75                  80

Tyr Pro Val Asp Asp His His Phe Lys Ile Ile Leu His Tyr Gly Thr
                85                  90                  95

Leu Val Ile Asp Gly Val Thr Pro Asn Met Ile Asp Tyr Phe Gly Arg
            100                 105                 110

Pro Tyr Pro Gly Ile Ala Val Phe Asp Gly Lys Gln Ile Thr Val Thr
        115                 120                 125

Gly Thr Leu Trp Asn Gly Asn Lys Ile Tyr Asp Glu Arg Leu Ile Asn
    130                 135                 140

Pro Asp Gly Ser Leu Leu Phe Arg Val Thr Ile Asn Gly Val Thr Gly
145                 150                 155                 160

Trp Arg Leu Cys Glu Asn Ile Leu Ala
                165

<210> SEQ ID NO 11
<211> LENGTH: 510
<212> TYPE: DNA
<213> ORGANISM: Artificial sequence
<220> FEATURE:
<223> OTHER INFORMATION: synthetic DNA
<220> FEATURE:
<221> NAME/KEY: CDS
<222> LOCATION: (1)..(510)

<400> SEQUENCE: 11 ttt acg ttg gca gat ttc gtt gga gac tgg caa cag aca gct gga tac    48
Phe Thr Leu Ala Asp Phe Val Gly Asp Trp Gln Gln Thr Ala Gly Tyr
1               5                   10                  15 aac caa gat caa gtg tta gaa caa gga gga ttg tct agt ctg ttc caa    96
Asn Gln Asp Gln Val Leu Glu Gln Gly Gly Leu Ser Ser Leu Phe Gln
            20                  25                  30 gcc ctg gga gtg tca gtc acg ccc ata cag aaa atc gta ctg tct ggg   144
Ala Leu Gly Val Ser Val Thr Pro Ile Gln Lys Ile Val Leu Ser Gly
        35                  40                  45 gag aat ggg tta aaa gct gat att cat gtc ata ata cct tac gag gga   192
Glu Asn Gly Leu Lys Ala Asp Ile His Val Ile Ile Pro Tyr Glu Gly
    50                  55                  60 ctc agt ggt ttt caa atg ggt cta att gaa atg atc ttc aaa gtt gtt   240
Leu Ser Gly Phe Gln Met Gly Leu Ile Glu Met Ile Phe Lys Val Val
65                  70                  75                  80
```

```
tac ccc gtg gat gat cat cat ttc aag att att ctc cat tat ggt aca    288
Tyr Pro Val Asp Asp His His Phe Lys Ile Ile Leu His Tyr Gly Thr
                85                  90                  95 ctc gtt att gac ggt gta aca ccc aac atg att gac tac ttt gga aga    336
Leu Val Ile Asp Gly Val Thr Pro Asn Met Ile Asp Tyr Phe Gly Arg
            100                 105                 110 cct tac cct gga att gct gta ttt gac ggc aag cag atc aca gtt act    384
Pro Tyr Pro Gly Ile Ala Val Phe Asp Gly Lys Gln Ile Thr Val Thr
        115                 120                 125 gga act ctg tgg aac ggc aac aag atc atc gat gag agg cta atc aac    432
Gly Thr Leu Trp Asn Gly Asn Lys Ile Ile Asp Glu Arg Leu Ile Asn
    130                 135                 140 cct gat ggt tca ctc ctc ttc aga gtt act atc aat gga gtc acg gga    480
Pro Asp Gly Ser Leu Leu Phe Arg Val Thr Ile Asn Gly Val Thr Gly
145                 150                 155                 160 tgg agg ctt tgc gag aac att ctt gcc taa                            510
Trp Arg Leu Cys Glu Asn Ile Leu Ala
                165

<210> SEQ ID NO 12
<211> LENGTH: 169
<212> TYPE: PRT
<213> ORGANISM: Artificial sequence
<220> FEATURE:
<223> OTHER INFORMATION: Synthetic Construct

<400> SEQUENCE: 12

Phe Thr Leu Ala Asp Phe Val Gly Asp Trp Gln Gln Thr Ala Gly Tyr
1               5                   10                  15

Asn Gln Asp Gln Val Leu Glu Gln Gly Gly Leu Ser Ser Leu Phe Gln
            20                  25                  30

Ala Leu Gly Val Ser Val Thr Pro Ile Gln Lys Ile Val Leu Ser Gly
        35                  40                  45

Glu Asn Gly Leu Lys Ala Asp Ile His Val Ile Ile Pro Tyr Glu Gly
    50                  55                  60

Leu Ser Gly Phe Gln Met Gly Leu Ile Glu Met Ile Phe Lys Val Val
65                  70                  75                  80

Tyr Pro Val Asp Asp His His Phe Lys Ile Ile Leu His Tyr Gly Thr
                85                  90                  95

Leu Val Ile Asp Gly Val Thr Pro Asn Met Ile Asp Tyr Phe Gly Arg
            100                 105                 110

Pro Tyr Pro Gly Ile Ala Val Phe Asp Gly Lys Gln Ile Thr Val Thr
        115                 120                 125

Gly Thr Leu Trp Asn Gly Asn Lys Ile Ile Asp Glu Arg Leu Ile Asn
    130                 135                 140

Pro Asp Gly Ser Leu Leu Phe Arg Val Thr Ile Asn Gly Val Thr Gly
145                 150                 155                 160

Trp Arg Leu Cys Glu Asn Ile Leu Ala
                165

<210> SEQ ID NO 13
<211> LENGTH: 510
<212> TYPE: DNA
<213> ORGANISM: Artificial sequence
<220> FEATURE:
<223> OTHER INFORMATION: synthetic DNA
<220> FEATURE:
<221> NAME/KEY: CDS
<222> LOCATION: (1)..(510)
```

```
<400> SEQUENCE: 13 ttt acg ttg gca gat ttc gtt gga gac tgg caa cag aca gct gga tac        48
Phe Thr Leu Ala Asp Phe Val Gly Asp Trp Gln Gln Thr Ala Gly Tyr
1               5                   10                  15 aac caa gat caa gtg tta gaa caa gga gga ttg tct agt ctg ttc caa        96
Asn Gln Asp Gln Val Leu Glu Gln Gly Gly Leu Ser Ser Leu Phe Gln
            20                  25                  30 gcc ctg gga gtg tca gtc acg ccc ata cag aaa gtt gta ctg tct ggg       144
Ala Leu Gly Val Ser Val Thr Pro Ile Gln Lys Val Val Leu Ser Gly
        35                  40                  45 gag aat ggg tta aaa atc gat att cat gtc ata ata cct tac gag gga       192
Glu Asn Gly Leu Lys Ile Asp Ile His Val Ile Ile Pro Tyr Glu Gly
    50                  55                  60 ctc agt ggt ttt caa atg ggt cta att gaa atg atc ttc aaa gtt gtt       240
Leu Ser Gly Phe Gln Met Gly Leu Ile Glu Met Ile Phe Lys Val Val
65                  70                  75                  80 tac ccc gtg gat gat cat cat ttc aag att att ctc cat tat ggt aca       288
Tyr Pro Val Asp Asp His His Phe Lys Ile Ile Leu His Tyr Gly Thr
                85                  90                  95 ctc gtt att gac ggt gta aca ccc aac atg att gac tac ttt gga aga       336
Leu Val Ile Asp Gly Val Thr Pro Asn Met Ile Asp Tyr Phe Gly Arg
            100                 105                 110 cct tac cct gga att gct gta ttt gac ggc aag cag atc aca gtt act       384
Pro Tyr Pro Gly Ile Ala Val Phe Asp Gly Lys Gln Ile Thr Val Thr
        115                 120                 125 gga act ctg tgg aac ggc aac aag atc atc gat gag agg cta atc aac       432
Gly Thr Leu Trp Asn Gly Asn Lys Ile Ile Asp Glu Arg Leu Ile Asn
    130                 135                 140 cct gat ggt tca ctc ctc ttc aga gtt act atc aat gga gtc acg gga       480
Pro Asp Gly Ser Leu Leu Phe Arg Val Thr Ile Asn Gly Val Thr Gly
145                 150                 155                 160 tgg agg ctt tgc gag aac att ctt gcc taa                                510
Trp Arg Leu Cys Glu Asn Ile Leu Ala
                165

<210> SEQ ID NO 14
<211> LENGTH: 169
<212> TYPE: PRT
<213> ORGANISM: Artificial sequence
<220> FEATURE:
<223> OTHER INFORMATION: Synthetic Construct

<400> SEQUENCE: 14

Phe Thr Leu Ala Asp Phe Val Gly Asp Trp Gln Gln Thr Ala Gly Tyr
1               5                   10                  15

Asn Gln Asp Gln Val Leu Glu Gln Gly Gly Leu Ser Ser Leu Phe Gln
            20                  25                  30

Ala Leu Gly Val Ser Val Thr Pro Ile Gln Lys Val Val Leu Ser Gly
        35                  40                  45

Glu Asn Gly Leu Lys Ile Asp Ile His Val Ile Ile Pro Tyr Glu Gly
    50                  55                  60

Leu Ser Gly Phe Gln Met Gly Leu Ile Glu Met Ile Phe Lys Val Val
65                  70                  75                  80

Tyr Pro Val Asp Asp His His Phe Lys Ile Ile Leu His Tyr Gly Thr
                85                  90                  95

Leu Val Ile Asp Gly Val Thr Pro Asn Met Ile Asp Tyr Phe Gly Arg
            100                 105                 110

Pro Tyr Pro Gly Ile Ala Val Phe Asp Gly Lys Gln Ile Thr Val Thr
        115                 120                 125
```

```
Gly Thr Leu Trp Asn Gly Asn Lys Ile Ile Asp Glu Arg Leu Ile Asn
    130                 135                 140

Pro Asp Gly Ser Leu Leu Phe Arg Val Thr Ile Asn Gly Val Thr Gly
145                 150                 155                 160

Trp Arg Leu Cys Glu Asn Ile Leu Ala
                165

<210> SEQ ID NO 15
<211> LENGTH: 510
<212> TYPE: DNA
<213> ORGANISM: Artificial sequence
<220> FEATURE:
<223> OTHER INFORMATION: synthetic DNA
<220> FEATURE:
<221> NAME/KEY: CDS
<222> LOCATION: (1)..(510)

<400> SEQUENCE: 15 ttt acg ttg gca gat ttc gtt gga gac tgg caa cag aca gct gga tac        48
Phe Thr Leu Ala Asp Phe Val Gly Asp Trp Gln Gln Thr Ala Gly Tyr
1               5                   10                  15 aac caa gat caa gtg tta gaa caa gga gga ttg tct agt ctg ttc caa        96
Asn Gln Asp Gln Val Leu Glu Gln Gly Gly Leu Ser Ser Leu Phe Gln
            20                  25                  30 gcc ctg gga gtg tca gtc acg ccc ata cag aaa atc gta ctg tct ggg       144
Ala Leu Gly Val Ser Val Thr Pro Ile Gln Lys Ile Val Leu Ser Gly
        35                  40                  45 gag aat ggg tta aaa atc gat att cat gtc ata ata cct tac gag gga       192
Glu Asn Gly Leu Lys Ile Asp Ile His Val Ile Ile Pro Tyr Glu Gly
    50                  55                  60 ctc agt ggt ttt caa atg ggt cta att gaa atg atc ttc aaa gtt gtt       240
Leu Ser Gly Phe Gln Met Gly Leu Ile Glu Met Ile Phe Lys Val Val
65                  70                  75                  80 tac ccc gtg gat gat cat cat ttc aag att att ctc cat tat ggt aca       288
Tyr Pro Val Asp Asp His His Phe Lys Ile Ile Leu His Tyr Gly Thr
                85                  90                  95 ctc gtt att gac ggt gta aca ccc aac atg att gac tac ttt gga aga       336
Leu Val Ile Asp Gly Val Thr Pro Asn Met Ile Asp Tyr Phe Gly Arg
            100                 105                 110 cct tac cct gga att gct gta ttt gac ggc aag cag atc aca gtt act       384
Pro Tyr Pro Gly Ile Ala Val Phe Asp Gly Lys Gln Ile Thr Val Thr
        115                 120                 125 gga act ctg tgg aac ggc aac aag atc atc gat gag agg cta atc aac       432
Gly Thr Leu Trp Asn Gly Asn Lys Ile Ile Asp Glu Arg Leu Ile Asn
    130                 135                 140 cct gat ggt tca ctc ctc ttc aga gtt act atc aat gga gtc acg gga       480
Pro Asp Gly Ser Leu Leu Phe Arg Val Thr Ile Asn Gly Val Thr Gly
145                 150                 155                 160 tgg agg ctt tgc gag aac att ctt gcc taa                               510
Trp Arg Leu Cys Glu Asn Ile Leu Ala
                165

<210> SEQ ID NO 16
<211> LENGTH: 169
<212> TYPE: PRT
<213> ORGANISM: Artificial sequence
<220> FEATURE:
<223> OTHER INFORMATION: Synthetic Construct

<400> SEQUENCE: 16

Phe Thr Leu Ala Asp Phe Val Gly Asp Trp Gln Gln Thr Ala Gly Tyr
1               5                   10                  15
```

-continued

Asn Gln Asp Gln Val Leu Glu Gln Gly Gly Leu Ser Ser Leu Phe Gln
            20                  25                  30

Ala Leu Gly Val Ser Val Thr Pro Ile Gln Lys Ile Val Leu Ser Gly
        35                  40                  45

Glu Asn Gly Leu Lys Ile Asp Ile His Val Ile Pro Tyr Glu Gly
50                  55                  60

Leu Ser Gly Phe Gln Met Gly Leu Ile Glu Met Ile Phe Lys Val Val
65                  70                  75                  80

Tyr Pro Val Asp Asp His His Phe Lys Ile Ile Leu His Tyr Gly Thr
                85                  90                  95

Leu Val Ile Asp Gly Val Thr Pro Asn Met Ile Asp Tyr Phe Gly Arg
            100                 105                 110

Pro Tyr Pro Gly Ile Ala Val Phe Asp Gly Lys Gln Ile Thr Val Thr
        115                 120                 125

Gly Thr Leu Trp Asn Gly Asn Lys Ile Ile Asp Glu Arg Leu Ile Asn
130                 135                 140

Pro Asp Gly Ser Leu Leu Phe Arg Val Thr Ile Asn Gly Val Thr Gly
145                 150                 155                 160

Trp Arg Leu Cys Glu Asn Ile Leu Ala
                165

<210> SEQ ID NO 17
<211> LENGTH: 19
<212> TYPE: DNA
<213> ORGANISM: Artificial sequence
<220> FEATURE:
<223> OTHER INFORMATION: synthetic DNA

<400> SEQUENCE: 17
acgccatatc gccgaaagg                                              19

<210> SEQ ID NO 18
<211> LENGTH: 27
<212> TYPE: DNA
<213> ORGANISM: Artificial sequence
<220> FEATURE:
<223> OTHER INFORMATION: synthetic DNA

<400> SEQUENCE: 18
taacacttga tctaggttgt atccagc                                     27

<210> SEQ ID NO 19
<211> LENGTH: 27
<212> TYPE: DNA
<213> ORGANISM: Artificial sequence
<220> FEATURE:
<223> OTHER INFORMATION: synthetic DNA

<400> SEQUENCE: 19
gctggataca acctagatca agtgtta                                     27

<210> SEQ ID NO 20
<211> LENGTH: 37
<212> TYPE: DNA
<213> ORGANISM: Artificial sequence
<220> FEATURE:
<223> OTHER INFORMATION: synthetic DNA

<400> SEQUENCE: 20
ccgctctaga ttaggcaaga atgttctcgc aaagcct                          37

<210> SEQ ID NO 21
<211> LENGTH: 33
<212> TYPE: DNA
<213> ORGANISM: Artificial sequence
<220> FEATURE:
<223> OTHER INFORMATION: synthetic DNA

<400> SEQUENCE: 21
gcggaattct ttacgttggc agatttcgtt gga            33

<210> SEQ ID NO 22
<211> LENGTH: 36
<212> TYPE: DNA
<213> ORGANISM: Artificial sequence
<220> FEATURE:
<223> OTHER INFORMATION: synthetic DNA

<400> SEQUENCE: 22
ccggaattct ttacgctgga ggatttcgtt ggagac         36

<210> SEQ ID NO 23
<211> LENGTH: 53
<212> TYPE: DNA
<213> ORGANISM: Artificial sequence
<220> FEATURE:
<223> OTHER INFORMATION: synthetic DNA

<400> SEQUENCE: 23
ccggaattct ttacgttggc agatttcgtt ggagactggc gacagacagc tgg    53

<210> SEQ ID NO 24
<211> LENGTH: 27
<212> TYPE: DNA
<213> ORGANISM: Artificial sequence
<220> FEATURE:
<223> OTHER INFORMATION: synthetic DNA

<400> SEQUENCE: 24
gaacagacta gacactcctc cttgttc                   27

<210> SEQ ID NO 25
<211> LENGTH: 27
<212> TYPE: DNA
<213> ORGANISM: Artificial sequence
<220> FEATURE:
<223> OTHER INFORMATION: synthetic DNA

<400> SEQUENCE: 25
gaacaaggag gagtgtctag tctgttc                   27

<210> SEQ ID NO 26
<211> LENGTH: 27
<212> TYPE: DNA
<213> ORGANISM: Artificial sequence
<220> FEATURE:
<223> OTHER INFORMATION: synthetic DNA

<400> SEQUENCE: 26
tgacactccc aggttttgga acagact                   27

<210> SEQ ID NO 27
<211> LENGTH: 27
<212> TYPE: DNA
<213> ORGANISM: Artificial sequence
<220> FEATURE:
<223> OTHER INFORMATION: synthetic DNA

```
<400> SEQUENCE: 27
agtctgttcc aaaacctggg agtgtca                                        27

<210> SEQ ID NO 28
<211> LENGTH: 27
<212> TYPE: DNA
<213> ORGANISM: Artificial sequence
<220> FEATURE:
<223> OTHER INFORMATION: synthetic DNA

<400> SEQUENCE: 28
agacagtaca actctctgta tgggcgt                                        27

<210> SEQ ID NO 29
<211> LENGTH: 27
<212> TYPE: DNA
<213> ORGANISM: Artificial sequence
<220> FEATURE:
<223> OTHER INFORMATION: synthetic DNA

<400> SEQUENCE: 29
acgcccatac agagagttgt actgtct                                        27

<210> SEQ ID NO 30
<211> LENGTH: 27
<212> TYPE: DNA
<213> ORGANISM: Artificial sequence
<220> FEATURE:
<223> OTHER INFORMATION: synthetic DNA

<400> SEQUENCE: 30
cccagacagt actattttct gtatggg                                        27

<210> SEQ ID NO 31
<211> LENGTH: 27
<212> TYPE: DNA
<213> ORGANISM: Artificial sequence
<220> FEATURE:
<223> OTHER INFORMATION: synthetic DNA

<400> SEQUENCE: 31
cccatacaga aaatagtact gtctggg                                        27

<210> SEQ ID NO 32
<211> LENGTH: 27
<212> TYPE: DNA
<213> ORGANISM: Artificial sequence
<220> FEATURE:
<223> OTHER INFORMATION: synthetic DNA

<400> SEQUENCE: 32
gacatgaata tcgattttta acccatt                                        27

<210> SEQ ID NO 33
<211> LENGTH: 27
<212> TYPE: DNA
<213> ORGANISM: Artificial sequence
<220> FEATURE:
<223> OTHER INFORMATION: synthetic DNA

<400> SEQUENCE: 33
aatgggttaa aaatcgatat tcatgtc                                        27

<210> SEQ ID NO 34
```

```
<211> LENGTH: 21
<212> TYPE: DNA
<213> ORGANISM: Artificial sequence
<220> FEATURE:
<223> OTHER INFORMATION: synthetic DNA

<400> SEQUENCE: 34
tggcagggat cttagattct g                                              21

<210> SEQ ID NO 35
<211> LENGTH: 27
<212> TYPE: DNA
<213> ORGANISM: Artificial sequence
<220> FEATURE:
<223> OTHER INFORMATION: synthetic DNA

<400> SEQUENCE: 35
tagacccatt tgatcaccac tgagtcc                                        27

<210> SEQ ID NO 36
<211> LENGTH: 27
<212> TYPE: DNA
<213> ORGANISM: Artificial sequence
<220> FEATURE:
<223> OTHER INFORMATION: synthetic DNA

<400> SEQUENCE: 36
ggactcagtg gtgatcaaat gggtcta                                        27

<210> SEQ ID NO 37
<211> LENGTH: 27
<212> TYPE: DNA
<213> ORGANISM: Artificial sequence
<220> FEATURE:
<223> OTHER INFORMATION: synthetic DNA

<400> SEQUENCE: 37
gatcatttca atttgaccca tttgaaa                                        27

<210> SEQ ID NO 38
<211> LENGTH: 27
<212> TYPE: DNA
<213> ORGANISM: Artificial sequence
<220> FEATURE:
<223> OTHER INFORMATION: synthetic DNA

<400> SEQUENCE: 38
tttcaaatgg gtcaaattga aatgatc                                        27

<210> SEQ ID NO 39
<211> LENGTH: 27
<212> TYPE: DNA
<213> ORGANISM: Artificial sequence
<220> FEATURE:
<223> OTHER INFORMATION: synthetic DNA

<400> SEQUENCE: 39
aactttgaag atcttttcaa ttagacc                                        27

<210> SEQ ID NO 40
<211> LENGTH: 27
<212> TYPE: DNA
<213> ORGANISM: Artificial sequence
<220> FEATURE:
<223> OTHER INFORMATION: synthetic DNA

<400> SEQUENCE: 40
```
ggtctaattg aaaagatctt caaagtt                                              27

<210> SEQ ID NO 41
<211> LENGTH: 27
<212> TYPE: DNA
<213> ORGANISM: Artificial sequence
<220> FEATURE:
<223> OTHER INFORMATION: synthetic DNA

<400> SEQUENCE: 41
ataatggaga ataaccttga aatgatg                                              27

<210> SEQ ID NO 42
<211> LENGTH: 27
<212> TYPE: DNA
<213> ORGANISM: Artificial sequence
<220> FEATURE:
<223> OTHER INFORMATION: synthetic DNA

<400> SEQUENCE: 42
catcatttca aggttattct ccattat                                              27

<210> SEQ ID NO 43
<211> LENGTH: 27
<212> TYPE: DNA
<213> ORGANISM: Artificial sequence
<220> FEATURE:
<223> OTHER INFORMATION: synthetic DNA

<400> SEQUENCE: 43
tacagcaatt ccttcgtaag gtcttcc                                              27

<210> SEQ ID NO 44
<211> LENGTH: 27
<212> TYPE: DNA
<213> ORGANISM: Artificial sequence
<220> FEATURE:
<223> OTHER INFORMATION: synthetic DNA

<400> SEQUENCE: 44
ggaagacctt acgaaggaat tgctgta                                              27

<210> SEQ ID NO 45
<211> LENGTH: 27
<212> TYPE: DNA
<213> ORGANISM: Artificial sequence
<220> FEATURE:
<223> OTHER INFORMATION: synthetic DNA

<400> SEQUENCE: 45
agtaactgtg atcttcttgc cgtcaaa                                              27

<210> SEQ ID NO 46
<211> LENGTH: 27
<212> TYPE: DNA
<213> ORGANISM: Artificial sequence
<220> FEATURE:
<223> OTHER INFORMATION: synthetic DNA

<400> SEQUENCE: 46
tttgacggca agaagatcac agttact                                              27

<210> SEQ ID NO 47
<211> LENGTH: 27
<212> TYPE: DNA

<213> ORGANISM: Artificial sequence
<220> FEATURE:
<223> OTHER INFORMATION: synthetic DNA

<400> SEQUENCE: 47
tagcctctca tcaatgatct tgttgcc                                     27

<210> SEQ ID NO 48
<211> LENGTH: 27
<212> TYPE: DNA
<213> ORGANISM: Artificial sequence
<220> FEATURE:
<223> OTHER INFORMATION: synthetic DNA

<400> SEQUENCE: 48
ggcaacaaga tcattgatga gaggcta                                     27

<210> SEQ ID NO 49
<211> LENGTH: 33
<212> TYPE: DNA
<213> ORGANISM: Artificial sequence
<220> FEATURE:
<223> OTHER INFORMATION: synthetic DNA

<400> SEQUENCE: 49
gcctctagat taggcaagaa tcctctcgca aag                              33

<210> SEQ ID NO 50
<211> LENGTH: 33
<212> TYPE: DNA
<213> ORGANISM: Artificial sequence
<220> FEATURE:
<223> OTHER INFORMATION: synthetic DNA

<400> SEQUENCE: 50
gcggaattct tcaccctgga ggacttcgtc ggc                              33

<210> SEQ ID NO 51
<211> LENGTH: 36
<212> TYPE: DNA
<213> ORGANISM: Artificial sequence
<220> FEATURE:
<223> OTHER INFORMATION: synthetic DNA

<400> SEQUENCE: 51
gcctctagat taggccagga ttctctcgca cagtct                           36

<210> SEQ ID NO 52
<211> LENGTH: 30
<212> TYPE: DNA
<213> ORGANISM: Artificial sequence
<220> FEATURE:
<223> OTHER INFORMATION: synthetic DNA

<400> SEQUENCE: 52
ggcgaattcg gtgggcttgg cctcggccac                                  30

<210> SEQ ID NO 53
<211> LENGTH: 20
<212> TYPE: DNA

```
<213> ORGANISM: Artificial sequence
<220> FEATURE:
<223> OTHER INFORMATION: synthetic DNA

<400> SEQUENCE: 53
taatacgact cactataggg                                              20
```

MUTATED GENES FOR THE CATALYTIC PROTEIN OF *OPLOPHORUS* LUCIFERASE AND USE THEREOF

This application claims benefit of the priority application, Japanese patent application no. 2013-218111, filed on Oct. 21, 2013, which is incorporated by reference herein in its entirety.

SEQUENCE LISTING

The instant application contains a sequence listing which has been submitted in ASCII format via EFS-Web and is hereby incorporated by reference in its entirety. Said ASCII copy, created on Oct. 9, 2014 is named G1212_Sequence_Listings_101014_F.txt and is 40,975 bytes in size.

TECHNICAL FIELD

The present invention relates to mutated genes for the catalytic protein of *Oplophorus* luciferase use thereof and so on.

BACKGROUND OF INVENTION

Bioluminescence is a phenomenon based on a chemical reaction in vivo, which is called a luciferin (a luminescence substrate)-luciferase (an enzyme that catalyzes the luminescence reaction) reaction. Numerous studies of the identification of luciferins or luciferases and the elucidation of the luminescence mechanism in a molecular level have been performed for a long time in the country and overseas. In bioluminescent marine organisms, *Oplophorus gracilirostris* luciferase from the deep-sea shrimp is an extracellularly secreted luciferase (Non-Patent Document 1). *Oplophorus* luciferase is a 106 kDa protein composed of a protein with a molecular weight of 35 kDa and a protein with a molecular weight of 19 kDa. The domain that catalyzes the luminescence reaction is found to be 19 kDa protein. *Oplophorus* luciferase uses coelenterazine as a luminescence substrate and is classified as a coelenterazine-type luciferase (Patent Document 1, Non-Patent Document 2). *Oplophorus* luciferase is different from other coelenterazine-type luciferases in broad substrate specificity and uses coelenterazine analogues as a suitable substrate as well as coelenterazine (Non-Patent Document 2). When the gene for the 19 kDa protein is expressed in *Escherichia coli* (*E. coli*) at ordinary and lower temperatures, the protein is expressed mostly as an insoluble protein (Non-Patent Document 3). When the 19 kDa protein was expressed as a fusion protein to ZZ domain from protein A in a low temperature expression system, the fused protein could be expressed as a soluble protein (Non-Patent Document 4). It is reported that when the 19 kDa protein was expressed in animal cultured cells, the expressed protein was hardly secreted outside of cells (Non-Patent Document 2).

Recently, it is reported that the mutated 19 kDa protein having catalytic activity of luminescence was prepared by mutating the 16 amino acids of the 19 kDa protein and showed higher luminescence activity than native 19 kDa protein, and was secreted into an extracellular medium (Patent Document 2, Non-Patent Documents 4 and 5). It is also reported that coelenterazine derivatives displayed higher activity than native coelenterazine used as a substrate (Non-Patent Documents 4 and 5).

In the luminescence reaction system using coelenterazine as a substrate for the luminescence reaction, the luminescence reaction of luciferasae proceeds only by a substrate and molecular oxygen. For this reason, a coelenterazine-type luciferase gene is used widely as a reporter assay in an animal cultured cell system at present. *Renilla* luciferase having 311 amino acids is used for a reporter assay inside of cells. For an extracellular reporter assay, the secretory *Gaussia* luciferase having 168 amino acids is used. Comparison in specific activity between recombinant *Renilla* luciferase and recombinant *Gaussia* luciferase using coelenterazine as a substrate reveals that the specific activity of *Renilla* luciferase is about $1/100$ of *Gaussia* luciferase (Non-Patent Documents 5 and 6). On the other hand, the specific activity of the mutated 19 kDa protein which catalyzes the luminescence reaction is $1/10$ of *Gaussia* luciferase and the mutated 19 kDa protein was found to be obviously inferior as a reporter assay gene as a secretory protein by comparison with *Gaussia* luciferase.

In view of the foregoing, there has been desired a reporter gene that is a luciferase expressed intracellularly and exhibits higher luminescence activity than wild 19 kDa protein, when not only coelenterazine but its analogue is used as a substrate.

RELATED ART DOCUMENTS

Patent Documents

[Patent Document 1] Japanese Patent No. 4613441
[Patent Document 2] Japanese National Publication (Tokuhyo) No. 2012-525819

Non-Patent Documents

[Non-Patent Document 1] O. Shimomura et al. (1978) Biochemistry 17: 994-998.
[Non-Patent Document 2] S. Inouye et al. (2000) FEBS Lett. 481: 19-25.
[Non-Patent Document 3] S. Inouye & S. Sasaki (2007) Protein Express. Purif. 56: 261-268.
[Non-Patent Document 4] M. P. Hall et al. (2012) ACS Chem. Biol. 7: 1848-1857.
[Non-Patent Document 5] S. Inouye et al. (2013) Biochem. Biophys. Res. Commun. 437: 23-28.
[Non-Patent Document 6] S. Inouye et al. (2013) Protein Express. Purif. 88: 150-156.

DISCLOSURE OF THE INVENTION

Problems to be Solved by the Invention

Under the foregoing circumstances, a novel luciferase that is distinct from conventional luciferases has been desired.

Means for Solving the Problem

The present inventors have made extensive investigations to solve the problem above and examined all of the mutated positions in the known mutated 19 kDa protein which catalyzes luminescence reaction. As a result, the inventors have newly produced the luciferase mutants by the method of selection and combination of the mutations, which have higher activity than the known mutated 19 kDa protein having catalytic activity of luminescence and are hardly secreted extracellularly when expressed in animal cultured cells. The present invention has thus been accomplished.

More specifically, the present invention provides the following luciferase mutants, polynucleotides, recombinant vectors, transformants, a method of producing luciferase mutants, kits, a method of performing a luminescence reaction, and so on.

[1] A luciferase mutant defined in (a) or (b) below:

(a) a luciferase mutant comprising an amino acid sequence in which at least one amino acid selected from the group consisting of valine at the position of 44, alanine at the position of 54 and tyrosine at the position of 138 is substituted with other amino acid(s) in the amino acid sequence of SEQ ID NO: 2; or, (b) a luciferase mutant comprising an amino acid sequence in which at least one amino acid selected from the group consisting of valine at the position of 44, alanine at the position of 54 and tyrosine at the position of 138 is substituted with other amino acid(s) and one or more amino acids are substituted with other amino acid(s) at position(s) except for the positions of 4, 11, 18, 27, 33, 43, 68, 72, 75, 90, 115, 124 and 166 in the amino acid sequence of SEQ ID NO: 2, and having luciferase activity.

[2] The luciferase mutant according to [1] above, wherein said luciferase mutant defined in (b) above is (c) below:

(c) a luciferase mutant comprising an amino acid sequence of SEQ ID NO. 2 in which at least one amino acid selected from the group consisting of valine at the position of 44, alanine at the position of 54 and tyrosine at the position of 138 is substituted with other amino acid(s) and 1 to 16 amino acids is/are substituted with other amino acid(s) at position(s) except for the positions of 4, 11, 18, 27, 33, 43, 68, 72, 75, 90, 115, 124 and 166, and having luciferase activity

[3] The luciferase mutant according to [1] or [2] above, wherein the other amino acid(s) which is/are substituted for at least one amino acid selected from the group consisting of valine at the position of 44, alanine at the position of 54 and tyrosine at the position of 138 is/are isoleucine.

[4] The luciferase mutant according to [1] above, wherein the protein defined in (a) above comprises an amino acid sequence of SEQ ID NO: 16, SEQ ID NO: 14, SEQ ID NO: 12, SEQ ID NO: 10, SEQ ID NO: 8, SEQ ID NO: 6 or SEQ ID NO: 4.

[5] A polynucleotide comprising a polynucleotide encoding the luciferase mutant according to any one of [1] to [4] above.

[6] A recombinant vector comprising the polynucleotide according to [5] above.

[7] A transformant transformed with the recombinant vector according to [6] above.

[8] A method of producing the luciferase mutant according to any one of [1] to [4] above, which comprises the steps of culturing the transformant of [7] above and producing the luciferase mutant according to any one of [1] to [4] above.

[9] A kit comprising at least one selected from the luciferase mutant according to any one of [1] to [4] above, the polynucleotide according to [5] above, the recombinant vector according to [6] above and the transformant according to [7] above.

[10] The kit according to [9] above, further comprising a luciferin.

[11] The kit according to [10] above, wherein the luciferin is coelenterazines.

[12] The kit according to [11] above, wherein the coelenterazines is coelenterazine.

[13] A method for performing a luminescence reaction, which comprises contacting the luciferase mutant according to any one of [1] to [4] above with a luciferin.

[14] The method according to [13] above, wherein the luciferin is coelenterazines.

[15] The method according to [14] above, wherein the coelenterazines is coelenterazine.

[16] A method for assaying activity of a sequence associated with the regulation of a promoter, which comprises using the polynucleotide according to [5] above as a reporter gene and contacting a luciferase mutant encoded by the reporter gene with a luciferin.

[17] The method according to [16] above, wherein the luciferin is coelenterazines.

[18] The method according to [17] above, wherein the coelenterazines is coelenterazine.

Effects of the Invention

The present invention provides luciferase mutants that are different from the known ones. In a preferred embodiment of the invention, the luciferase mutants have at least one property selected from the properties having higher luminescence activity than that of native 19 kDa protein and/or the known mutated 19 kDa protein capable of catalyzing luminescence reaction when coelenterazine and its analogues were used as a substrate, and little extracellular secretion when expressed in animal cells, and so on.

BRIEF DESCRIPTION OF DRAWINGS

The patent or application file contains at least one drawing executed in color. Copies of this patent or patent application publication with color drawing(s) will be provided by the Office upon request and payment of the necessary fee.

MODE FOR CARRYING OUT THE INVENTION

Figure 1:
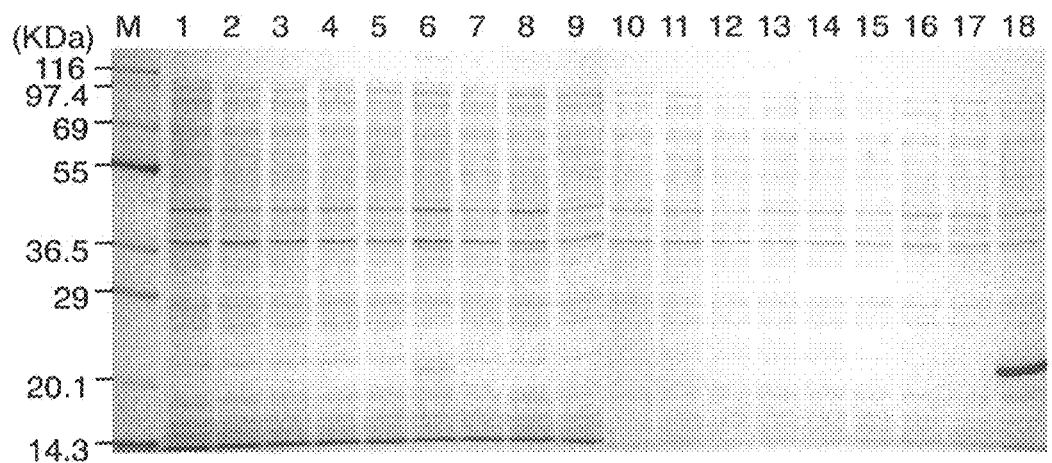
FIG. 1 shows the results of SDS-PAGE analysis of the supernatant and precipitate fractions from the crude enzyme solution (crude extract) of *E. coli* in which the KAZ mutants were expressed using pCold II vector.
Figure 1:
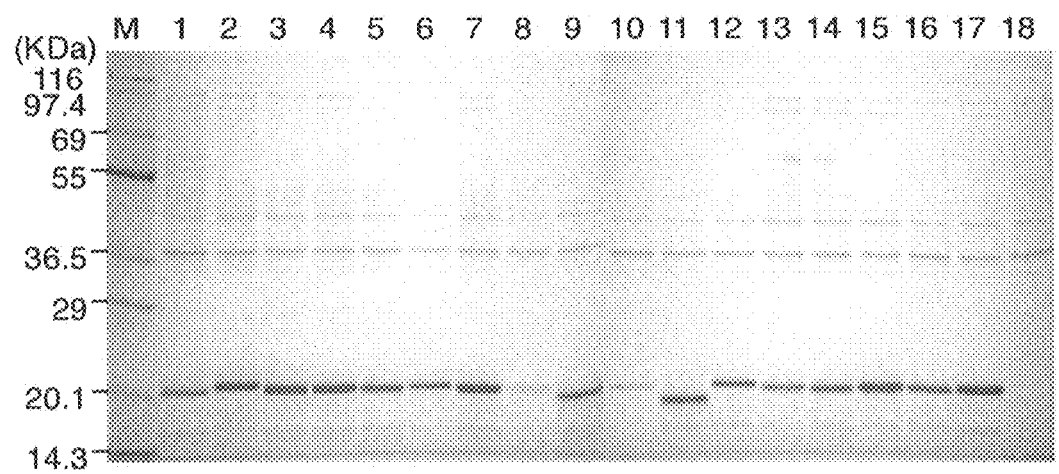

The present invention will be described below in detail.
1. Luciferase Mutants of the Invention The term luciferase mutant in the present invention refers to a mutant of the protein with a molecular weight of 19 kDa of *Oplophorus* luciferase. Specifically, the luciferase mutant of the present invention is intended to mean a luciferase mutant having substantially the same activity as the luciferase mutant comprising an amino acid sequence in which at least one amino acid selected from the group consisting of valine at the position of 44, alanine at the position of 54 and tyrosine at the position of 138 in the amino acid sequence of SEQ ID NO: 2 is substituted with other amino acid(s).

The term substantially the same activity is intended to mean at least one activity selected from luciferase activity, activity with little extracellular secretion when expressed in animal cells, and so on.

The term "luciferase activity" is intended to mean the activity for catalyzing the luminescence reaction using a luciferin (e.g., coelenterazines) which serves as a substrate, namely, the reaction in which luciferin (e.g., coelenterazines) is oxidized with molecular oxygen to produce oxyluciferin in its excited state. The excited state of oxyluciferin produced emits visible light and converts to the ground state.

Luminescence activity can be determined by the method described in, e.g., Inouye, S. & Shimomura, O. (1977) Biochem. Biophys. Res. Commun. 233, 349-353. Specifically, the luciferase mutant of the present invention is mixed with a luciferin to start the luminescence reaction, and the activity of catalyzing luminescence reaction can be determined using a luminometer. Commercially available luminometers, e.g., Luminescencer-PSN AB2200 (manufactured by Atto Corp.) or Centro 960 Luminometer (manufactured by Berthold Inc.) may be used as luminometers.

The luciferin used in the present invention may be any luciferin as far as it serves as a substrate for the luciferase mutants of the present invention. Specifically, the luciferin used in the present invention includes coelenterazines containing the imidazopyrazinone ring as the backbone.

The term coelenterazines are used to mean coelenterazine or its analogues. Coelenterazine analogues include, for example, bis-coelenterazine, deoxyfuran-coelenterazine (furimazine)), h-coelenterazine, hcp-coelenterazine, cp-coelenterazine, f-coelenterazine, fcp-coelenterazine, n-coelenterazine, MeO-coelenterazine, e-coelenterazine, cl-coelenterazine, ch-coelenterazine, 3 iso-coelenterazine, 3meo-coelenterazine, cf3-coelenterazine, i-coelenterazine, et-coelenterazine, me-coelenterazine, 3me-coelenterazine, αmeh-coelenterazine, 8-(1-naphthyl)-coelenterazine, 8-(2-naphthyl)-coelenterazine, 8-(2-thienyl)-coelenterazine, 6,8-di-(2-thienyl)-coelenterazine, 8-(4-hydroxyphenyl)-coelenterazine, 8-(2-benzothienyl)-coelenterazine, 8-(b-styryl)-coelenterazine, 8-phenyl-coelenterazine, 6-deoxy-coelenterazine, 8-(3-thienyl)-coelenterazine, and 8-(3-benzo[b]thienyl)-coelenterazine. Of these coelenterazines, coelenterazine is particularly preferred in the present invention.

These coelenterazines may be synthesized by publicly known methods or may also be commercially available.

The coelenterazines may be synthesized by the methods described in, e.g., Shimomura et al. (1988) Biochem. J. 251, 405-410, Shimomura et al. (1989) Biochem. J. 261, 913-920, Shimomura et al. (1990) Biochem. J. 270, 309-312, Tetrahedron Lett. 38: 6405-6406, WO 2010/090319, or Inouye et al. (2010) Anal. Biochem. 407, 247-252, or respective modifications thereof. Furimazine may be produced by the method described in Hall et al. (2012) ACS Chem. Biol. 16; 848-1857.

The coelenterazines which are commercially available include, for example, coelenterazine, cf3-coelenterazine and h-coelenterazine manufactured by JNC Corp.; hcp-coelenterazine, cp-coelenterazine, f-coelenterazine, fcp-coelenterazine and n-coelenterazine manufactured by Biotium Inc.; and coelenterazine, furimazine and h-coelenterazine manufactured by Promega Corp.

The "activity for catalyzing luminescence reaction using a luciferin which serves as a substrate" is activity for catalyzing luminescence reaction preferably using coelenterazines whish serves as a substrate. The "activity for catalyzing luminescence using coelenterazines as a substrate" is activity for catalyzing luminescence reaction preferably using coelenterazine which serves as a substrate.

The "activity with little extracellular secretion when expressed in animal cells" is intended to mean that when expressed in animal cells, a large part of the expressed protein is not transported but retained in the cells and hardly secreted outside the cells. Specifically, the "hardly secreted outside of cells" is intended to mean that the expressed protein is secreted outside the cells only in a trace amount (weight) of less than 5%, 4%, 3%, 2%, 1%, 0.5%, 0.1%, 0.05%, 0.01% or 0.005%. The "animal cells" include those later described.

The "luciferase mutant having substantially the same activity as the luciferase mutant comprising an amino acid sequence in which at least one amino acid selected from the group consisting of valine at the position of 44, alanine at the position of 54 and tyrosine at the position of 138 in the amino acid sequence of SEQ ID NO: 2 is substituted with other amino acid(s)" is, for example, the luciferase mutant described (a) or (b) below.

(a) A luciferase mutant comprising an amino acid sequence in which at least one amino acid selected from the group consisting of valine at the position of 44, alanine at the position of 54 and tyrosine at the position of 138 is substituted with different (or other) amino acid(s) in the amino acid sequence of SEQ ID NO: 2;

(b) a luciferase mutant comprising an amino acid sequence in which at least one amino acid selected from the group consisting of valine at the position of 44, alanine at the position of 54 and tyrosine at the position of 138 is substituted with other amino acid(s) and one or more amino acids are substituted with other amino acid(s) at position(s) except for the positions of 4, 11, 18, 27, 33, 43, 68, 72, 75, 90, 115, 124 and 166 in the amino acid sequence of SEQ ID NO: 2, and having luciferase activity.

In (a) and (b) above, the term "at least one amino acid is substituted with other amino acid(s)" is intended to mean a substitution of at least one amino acid at 1 to 3 position(s) selected from the positions of 44, 54 and 138 in the amino acid sequence of SEQ ID NO: 2.

Specifically, "at least one" in "at least one amino acid is substituted with other amino acid(s)" is 1, 2 or 3, preferably 2 or 3, and more preferably 3.

The other amino acid which is substituted for valine at the position of 44 in the amino acid sequence of SEQ ID NO: 2 includes, for example, isoleucine, alanine, methionine, leucine, cysteine, serine and phenylalanine, preferably, isoleucine, alanine, methionine, leucine and cysteine, and more preferably, isoleucine.

The other amino acid which is substituted for alanine at the position of 54 in the amino acid sequence of SEQ ID NO: 2 is, for example, isoleucine, valine, methionine, leucine, cysteine, serine or phenylalanine, preferably, isoleucine, valine, methionine, leucine or cysteine, and more preferably, isoleucine.

The other amino acid which is substituted for tyrosine at the position of 138 in the amino acid sequence of SEQ ID NO: 2 is, for example, isoleucine, valine, leucine, methionine, cysteine, threonine, arginine, lysine, histidine or glutamine, preferably, isoleucine, valine, leucine, methionine, arginine or lysine, and more preferably, isoleucine.

The other amino acid(s) which is/are substituted for at least one amino acid selected from the group consisting of valine at the position of 44, alanine at the position of 54 and tyrosine at the position of 138 in the amino acid sequence of SEQ ID NO: 2 is/are preferably isoleucine.

In (b) above, the term "one or more amino acids are substituted with other amino acid(s)" is intended to mean that one or more substitutions occur at optional and one or more positions in the same amino acid sequence.

The range of "one or more" in "one or more amino acids are substituted with other amino acids" is, for example, 1 to 35, 1 to 34, 1 to 33, 1 to 32, 1 to 31, 1 to 30, 1 to 29, 1 to 28, 1 to 27, 1 to 26, 1 to 25, 1 to 24, 1 to 23, 1 to 22, 1 to 21, 1 to 20, 1 to 19, 1 to 18, 1 to 17, 1 to 16, 1 to 15, 1 to 14, 1 to 13, 1 to 12, 1 to 11, 1 to 10, 1 to 9, 1 to 8, 1 to 7, 1 to 6 (1 to several), 1 to 5, 1 to 4, 1 to 3, 1 to 2 and 1. In general, the less the number of amino acids substituted, the more preferable. Such proteins may be produced by site-directed mutagenesis described in "Sambrook J. et al., Molecular Cloning: A Laboratory Manual, Third Edition, Cold Spring Harbor Laboratory Press (2001)," "Ausbel F. M. et al., Current Protocols in Molecular Biology, Supplement 1-38, John Wiley and Sons (1987-1997)," "Nuc. Acids. Res., 10, 6487 (1982)," "Proc. Natl. Acad. Sci. USA, 79, 6409 (1982)," "Gene, 34, 315 (1985)," "Nuc. Acids. Res., 13, 4431 (1985)," or "Proc. Natl. Acad. Sci. USA, 82, 488 (1985)," etc.

The position(s) of the amino acid(s) which is/are substituted in the amino acid sequence of SEQ ID NO: 2 is/are not particularly limited so long as the position(s) is/are other than the positions of 4, 11, 18, 27, 33, 43, 68, 72, 75, 90, 115, 124 and 166, in addition to the substitution positions of 44, 54 and 138 described above, and include one or more positions selected from the group consisting of the positions of 1, 2, 3, 13, 14, 15, 25, 30, 36, 70, 83, 106, 128, 153, 156, 157, 159, 162, 163 and 169, preferably, position(s) selected from the group consisting of the positions of 1, 2, 3, 13, 14, 153, 159, 163 and 169.

Examples of amino acid residues which are mutually substitutable are given below. Amino acid residues in the same group are mutually substitutable.

Group A: leucine, isoleucine, norleucine, valine, norvaline, alanine, 2-aminobutanoic acid, methionine, o-methylserine, t-butylglycine, t-butylalanine and cyclohexylalanine;
Group B: aspartic acid, glutamic acid, isoaspartic acid, isoglutamic acid, 2-aminoadipic acid and 2-aminosuberic acid;
Group C: asparagine and glutamine;
Group D: lysine, arginine, ornithine, 2,4-diaminobutanoic acid and 2,3-diaminopropionic acid;
Group E: proline, 3-hydroxyproline and 4-hydroxyproline;
Group F: serine, threonine and homoserine; and,
Group G: phenylalanine and tyrosine.

In a preferred embodiment of the invention, the luciferase mutant is a luciferase mutant comprising the amino acid sequence of SEQ ID NO: 16, SEQ ID NO: 14, SEQ ID NO: 12, SEQ ID NO: 10, SEQ ID NO: 8, SEQ ID NO: 6 or SEQ ID NO: 4, more preferably, a luciferase mutant comprising the amino acid sequence of SEQ ID NO: 16, SEQ ID NO: 14, SEQ ID NO: 12 or SEQ ID NO: 10, and most preferably, a luciferase mutant comprising the amino acid sequence of SEQ ID NO: 16.

The luciferase mutant of the present invention may further contain an additional peptide sequence at the N terminus and/or C terminus, preferably at the N terminus. The additional peptide sequence is at least one peptide sequence selected from the group consisting of a peptide sequence for purification, a peptide sequence for expressing the luciferase mutant of the present invention as a soluble protein and an epitope sequence capable of recognizing an antibody. The additional peptide sequence is preferably a peptide sequence for purification. In another preferred embodiment of the present invention, the additional peptide sequence is at least one sequence selected from the group consisting of a peptide sequence for purification and a peptide sequence for expressing the luciferase mutant of the present invention as a soluble protein.

Peptide sequences employed in the art may be used as the peptide sequence for purification. The peptide sequence for purification includes, for example, a histidine tag sequence having a consecutive amino acid sequence of at least 4 and preferably at least 6 histidine residues, an amino acid sequence with a binding domain of glutathione S-transferase into glutathione, the amino acid sequence of Protein A, etc.

The peptide used to express the luciferase mutant of the present invention as a soluble protein includes, for example, polypeptides represented by formula (Z)n. The amino acid sequences for the polypeptides represented by formula (Z)n and the nucleic acid sequences encoding the same are described in, e.g., JPA KOKAI No. 2008-99669.

Peptide sequences used in the art can be used as the epitope sequence capable of recognizing an antibody.

The method for acquiring the luciferase mutant of the invention is not particularly limited. The luciferase mutant of the invention may be a protein synthesized by chemical synthesis, or a recombinant protein produced by a genetic engineering technique. When the luciferase mutant of the invention is to be chemically synthesized, synthesis may be carried out by, for example, the Fmoc (fluorenylmethyloxycarbonyl) method or the tBoc (t-butyloxycarbonyl) method. In addition, peptide synthesizers available from Advanced ChemTech, PerkinElmer, Pharmacia, Protein Technology Instrument, Synthecell-Vega, PerSeptive, Shimadzu Corporation, etc. may also be used for chemical synthesis. When the luciferase mutant of the invention is to be produced by genetic engineering, the mutant may be produced by a conventional genetic recombination technique. More specifically, the luciferase mutant of the invention may be produced by inserting a polynucleotide (e.g., a DNA) encoding the luciferase mutant of the invention into a suitable expression system. The polynucleotide encoding the luciferase mutant of the invention, expression of the luciferase mutant of the invention in an expression system or the like will be later described.

2. Polynucleotide of the Invention

The present invention also provides a polynucleotide comprising a polynucleotide encoding the luciferase mutant of the invention described above. The polynucleotide of the invention may be any polynucleotide so long as it has a nucleotide sequence encoding the luciferase mutant of the invention, although a DNA is preferred. Examples of the DNA include genomic DNA, genomic DNA library, cellular or tissue cDNA, cellular or tissue cDNA library, synthetic DNA, etc. Vectors used in the libraries are not particularly limited and may be any of bacteriophages, plasmids, cosmids, phagemids, etc. Also, these vectors may be amplified directly by a Reverse Transcription Polymerase Chain Reaction (hereinafter abbreviated as RT-PCR) using the total RNA or mRNA fraction prepared from the cell or tissue described above.

The polynucleotide of the invention includes the following polynucleotides.

(i) A polynucleotide comprising a polynucleotide encoding the luciferase mutant comprising an amino acid sequence in which at least one amino acid selected from the group consisting of valine at the position of 44, alanine at the position of 54 and tyrosine at the position of 138 is substituted with other amino acid(s) in the amino acid sequence of SEQ ID NO: 2; or, (ii) A polynucleotide comprising a polynucleotide encoding the luciferase mutant comprising an amino acid sequence in which at least one amino acid selected from the group consisting of valine at the position of 44, alanine at the position of 54 and tyrosine at the position of 138 is substituted with other amino acid(s) and one or more amino acids are substituted with other amino acid(s) at position(s) except for the positions of 4, 11, 18, 27, 33, 43, 68, 72, 75, 90, 115, 124 and 166 in the amino acid sequence of SEQ ID NO: 2, and having luciferase activity.

The luciferase mutants of (i) and (ii) above are as described above.

A polynucleotide encoding a protein having a given amino acid sequence, in which one or more amino acids are substituted in the amino acid sequence, can be obtained by using a site-specific mutagenesis technique (see, e.g., Gotoh, T. et al., Gene 152, 271-275 (1995), Zoller, M. J., and Smith, M., Methods Enzymol. 100, 468-500 (1983), Kramer, W. et al., Nucleic Acids Res. 12, 9441-9456 (1984), Kramer W, and Fritz H. J., Methods. Enzymol. 154, 350-367 (1987), Kunkel, T. A., Proc. Natl. Acad. Sci. USA. 82, 488-492 (1985), Kunkel, Methods Enzymol. 85, 2763-2766 (1988); etc.), the methods using amber mutation (see, e.g., the gapped duplex method, Nucleic Acids Res., 12, 9441-9456 (1984), etc.), etc.

Alternatively, mutations can also be introduced into the polynucleotide by PCR (cf., e.g., Ho S, N. et al., Gene, 77, 51 (1989), etc.) using a pair of primers bearing on the respective 5' ends a sequence in which the targeted mutation (deletion, addition, substitution and/or insertion) has been introduced.

Also, a polynucleotide encoding a partial fragment of protein, which is one type of deletion mutant, can be obtained using as the primers an oligonucleotide having a sequence which matches the nucleotide sequence at the 5' end of the region encoding the partial fragment to be produced in the polynucleotide encoding the target protein and an oligonucleotide having a sequence complementary to the nucleotide sequence at the 3' end thereof, and performing PCR in which the polynucleotide encoding the target protein is used as a template.

The polynucleotide of the present invention includes preferably a polynucleotide comprising a polynucleotide encoding the luciferase mutant comprising the amino acid sequence of SEQ ID NO: 16, SEQ ID NO: 14, SEQ ID NO: 12, SEQ ID NO: 10, SEQ ID NO: 8, SEQ ID NO: 6 or SEQ ID NO: 4, more preferably, a polynucleotide comprising a polynucleotide encoding the luciferase mutant comprising the amino acid sequence of SEQ ID NO: 16, SEQ ID NO: 14, SEQ ID NO: 12 or SEQ ID NO: 10, and most preferably, a polynucleotide comprising a polynucleotide encoding the luciferase mutant comprising the amino acid sequence of SEQ ID NO: 16.

The polynucleotide encoding the luciferase mutant comprising the amino acid sequence of SEQ ID NO: 16 includes a polynucleotide comprising the nucleotide sequence of SEQ ID NO: 15. The polynucleotide encoding the luciferase mutant comprising the amino acid sequence of SEQ ID NO: 14 includes a polynucleotide comprising the nucleotide sequence of SEQ ID NO: 13. The polynucleotide encoding the luciferase mutant comprising the amino acid sequence of SEQ ID NO: 12 includes a polynucleotide comprising the nucleotide sequence of SEQ ID NO: 11. The polynucleotide encoding the luciferase mutant comprising the amino acid sequence of SEQ ID NO: 10 includes a polynucleotide comprising the nucleotide sequence of SEQ ID NO: 9. The polynucleotide encoding the luciferase mutant comprising the amino acid sequence of SEQ ID NO: 8 includes a polynucleotide comprising the nucleotide sequence of SEQ ID NO: 7. The polynucleotide encoding the luciferase mutant comprising the amino acid sequence of SEQ ID NO: 6 includes a polynucleotide comprising the nucleotide sequence of SEQ ID NO: 5. The polynucleotide encoding the luciferase mutant comprising the amino acid sequence of SEQ ID NO: 4 includes a polynucleotide comprising the nucleotide sequence of SEQ ID NO: 3.

In some embodiments of the present invention, the polynucleotide is preferably a polynucleotide comprising a polynucleotide consisting of the nucleotide sequence of SEQ ID NO: 15, SEQ ID NO: 13, SEQ ID NO: 11, SEQ ID NO: 9, SEQ ID NO: 7, SEQ ID NO: 5 or SEQ ID NO: 3, more preferably, a polynucleotide comprising a polynucleotide consisting of the nucleotide sequence of SEQ ID NO: 15, SEQ ID NO: 13, SEQ ID NO: 11 or SEQ ID NO: 9, and most preferably, a polynucleotide comprising a polynucleotide consisting of the nucleotide sequence of SEQ ID NO: 15.

The polynucleotide of the present invention may further contain a polynucleotide encoding an additional peptide sequence at the 5' end and/or 3' end, preferably at the 5' end. The polynucleotide encoding such an additional peptide sequence includes a polynucleotide encoding at least one peptide sequence selected from the group consisting of a peptide sequence for purification, a peptide sequence for expressing the luciferase mutant of the present invention as a soluble protein, an epitope sequence capable of recognizing an antibody, and the like.

Polynucleotides comprising nucleotide sequences encoding the peptide sequence for purification employed in the art can be used as the polynucleotide encoding the peptide sequence for purification. Examples of the peptide sequence for purification include those as described above.

The polynucleotide encoding the peptide sequence used to express the luciferase mutant of the present invention as a soluble protein includes, for example, polypeptides represented by formula (Z)n. The amino acid sequences for the polypeptides represented by formula (Z)n and the nucleic acid sequences encoding the same are those as described above.

Polynucleotides comprising nucleotide sequences encoding the epitope sequence capable of recognizing antibodies that are used in the art can be used as the polynucleotide encoding the antibody-recognizing epitope sequence.

3. Recombinant Vector and Transformant of the Invention

The present invention further provides recombinant vectors and transformants comprising the polynucleotides of the present invention described above.

Preparation of Recombinant Vector

The recombinant vector of the invention can be obtained by ligating (inserting) the polynucleotide (DNA) of the invention to (into) an appropriate vector. Specifically, the recombinant vector can be obtained by digesting the purified polynucleotide (DNA) with a suitable restriction enzyme, then inserting into a suitable vector at the restriction enzyme site or multicloning site, and ligating to the vector. The vector for inserting the polynucleotide of the invention is not particularly limited as long as it is replicable in a host, and includes plasmids, bacteriophages, animal viruses, etc. Examples of plasmids include plasmids from *E. coli* (e.g., pBR322, pBR325, pUC118, pUC119, etc.), plasmids from *Bacillus subtilis* (e.g., pUB110, pTP5, etc.) and plasmids from yeast (e.g., YEp13, YEp24, YCp50, etc.). Examples of bacteriophages include, e.g., λ phage. Examples of animal viruses include retroviruses, vaccinia viruses and insect viruses (e.g., baculoviruses). In addition, pCold I vector, pCold II vector, pCold III vector and pCold IV vector (all are manufactured by Takara Bio Inc.), pcDNA3 vector, PICZ vector (manufactured by Invitrogen Inc.) and the like may also be suitably used.

The polynucleotide of the present invention is generally ligated downstream to a promoter in a suitable vector in an expressible manner. When the host used for transformation is an animal cell, the promoter is preferably an SV40-derived promoter, retrovirus promoter, metallothionein promoter, heat shock promoter, cytomegalovirus promoter, SRα promoter, and so on. When the host is a bacterium of the genus *Escherichia*, Trp promoter, T7 promoter, lac promoter, recA promoter, λPL promoter, lpp promoter, etc. are preferred. When the host is a bacterium of the genus *Bacillus*, SPO1 promoter, SPO2 promoter, penP promoter, etc. are preferred. When the host is yeast, PHO5 promoter, PGK promoter, GAP promoter, ADH1 promoter, GAL promoter, etc. are preferred. When the host is an insect cell, polyhedrin promoter, P10 promoter, etc. are preferred.

A low-temperature expression-inducible promoter may also be suitably used. Examples of the low-temperature expression-inducible promoter include promoter sequences for cold shock genes. The cold shock gene includes, for example, *E. coli* cold shock genes (e.g., cspA, cspB, cspG, cspI and csdA), *Bacillus caldolyticus* cold shock genes (e.g., Bc-Csp), *Salmonella enterica* cold shock genes (e.g., cspE) and *Erwinia carotovora* cold shock genes (e.g., cspG). Among others, cspA promoter, cspB promoter, cspG promoter, cspI promoter, csdA promoter and the like can be advantageously used as the low-temperature expression-inducible promoter.

In addition to the foregoing, the recombinant vector of the invention may further contain, if desired, an enhancer, a splicing signal, a polyA addition signal, a ribosome binding sequence (SD sequence), a selection marker, etc., and provided for use. The selection marker includes, for example, a dihydrofolate reductase gene, an ampicillin resistance gene, a neomycin resistance gene, etc.

Preparation of Transformant

The thus obtained recombinant vector comprising the polynucleotide of the invention is introduced into an appropriate host to prepare the transformant. The host is not particularly limited as long as it is capable of expressing the polynucleotide (DNA) of the invention, and may be bacteria of the genera *Escherichia, Bacillus, Pseudomonas* and *Rhizobium*, yeast, animal cells or insect cells, etc. Bacteria of the genus *Escherichia* include *E. coli*, etc. Bacteria of the genus *Bacillus* include *Bacillus subtilis*, etc. Bacteria of the genus *Pseudomonas* include *Pseudomonas putida*, etc. Bacteria of the genus *Rhizobium* include *Rhizobium meliloti*, etc. Yeast includes *Saccharomyces cerevisiae, Schizosaccharomyces pombe*, etc. Animal cells include COS cells, CHO cells, HeLa cells, etc. Insect cells include Sf9, Sf21, etc.

The method of transfecting the recombinant vector into the host and the method of transformation by the same can be performed according to various general methods. The method for transfecting the recombinant vector into the host cell includes the calcium phosphate method (Virology, 52, 456-457 (1973)), the lipofection method (Proc. Natl. Acad. Sci. USA, 84, 7413 (1987)), the electroporation method (EMBO J., 1, 841-845 (1982)), etc. The method for transformation of the bacteria of the genus *Escherichia* includes the methods described in, e.g., Proc. Natl. Acad. Sci. USA, 69, 2110 (1972), Gene, 17, 107 (1982), etc. The method for transformation of the bacteria of the genus *Bacillus* includes the method described in Molecular & General Genetics, 168, 111 (1979), etc. The method for transforming yeast includes the method described in Proc. Natl. Acad. Sci. USA, 75, 1929 (1978), etc. The method for transformation of animal cells includes the method described in Virology, 52, 456 (1973), etc. The method for transformation of insect cells includes the method described in Bio/Technology, 6, 47-55 (1988), etc. Thus, the transformant transformed with the recombinant vector comprising the polynucleotide encoding the luciferase mutant of the invention (the polynucleotide of the invention) can be obtained.

Expression Vector and Transformant Comprising Low-Temperature Expression-Inducible Promoter Sequence An expression vector comprising the low-temperature expression-inducible promoter sequence is preferred as the expression vector among others.

Specifically, the expression vector comprising the low-temperature expression-inducible promoter sequence is intended to mean an expression vector comprising the following promoter sequence and coding sequence:

(1) a low-temperature expression-inducible promoter sequence; and,
(2) a coding sequence comprising the polynucleotide of the invention.

The low-temperature expression-inducible promoter sequence is intended to mean a promoter sequence which is capable of inducing expression of the protein by lowering the temperature from the culture conditions under which host cells can grow. Examples of the low-temperature expression-inducible promoter are promoters for genes encoding cold shock proteins (cold shock genes). Examples of the cold shock gene promoters include those as described above.

The temperature at which the low-temperature expression-inducible promoter used in the invention can induce expression is generally 30° C. or less, preferably 25° C. or less, more preferably 20° C. or less, and most preferably 15° C. or less. In order to induce the expression more efficiently, however, the expression induction is generally performed at 5° C. or more, preferably at 10° C. or more, and most preferably at approximately 15° C.

In preparing the expression vector of the invention comprising the low-temperature expression-inducible promoter sequence, the pCold I vector, pCold II vector, pCold III vector, and pCold IV vector (all manufactured by Takara Bio Inc.) can be suitably used as the vector for insertion of the polynucleotide of the invention. The protein can be produced as a soluble protein in the cytoplasm in a host cell when expressed in a prokaryotic host cell using these vectors.

Prokaryotic cells are preferred as the host into which the expression vector comprising the low-temperature expression-inducible promoter sequence is introduced, more preferably, *E. coli*, and particularly preferably, the BL21 and JM109 strains. Among others, the BL21 strain is most preferred.

Temperatures for incubation at which the transformant carrying the expression vector comprising the low-temperature expression-inducible promoter sequence grows are generally 25 to 40° C. and preferably 30 to 37° C. Temperatures for inducing the expression are generally 4 to 25° C., preferably 10 to 20° C., more preferably 12 to 18° C., and most preferably 15° C.

4. Production of Luciferase Mutant of the Invention

The present invention further provides a method for producing the luciferase mutant of the invention, which comprises the steps of culturing the transformant described above to produce the luciferase mutant of the invention. The luciferase mutant of the invention can be produced, for example, by culturing the transformant described above under conditions where the polynucleotide (DNA) encoding the luciferase mutant of the invention can be expressed, producing/accumulating and then separating/purifying the luciferase mutant of the invention.

Incubation of Transformant

The transformant of the invention may be incubated in a conventional manner used for incubation of a host. By the incubation, the luciferase mutant of the invention is produced from the transformant and accumulated in the transformant or in the culture medium.

The medium used for culturing the transformant using bacteria of the genus *Escherichia* or the genus *Bacillus* as a host may be any of a natural medium and a synthetic medium as far as it is a medium which contains carbon sources, nitrogen sources, inorganic salts, etc. necessary for growth of the transformant, and in which the transformant can efficiently grow. Examples of carbon sources which can be used are carbohydrates such as glucose, fructose, sucrose, starch, etc.; organic acids such as acetic acid, propionic acid, etc.; alcohols such as ethanol, propanol, and the like. Examples of nitrogen sources which can be used include ammonia, ammonium salts of inorganic or organic acids such as ammonium chloride, ammonium sulfate, ammonium acetate, ammonium phosphate, etc., and other nitrogen-containing compounds, and further include peptone, meat extracts, corn steep liquor, and the like. Examples of inorganic salts include monobasic potassium phosphate, dibasic potassium phosphate, magnesium phosphate, magnesium sulfate, sodium chloride, ferrous sulfate, manganese sulfate, copper sulfate, calcium carbonate, etc. If necessary, antibiotics such as ampicillin or tetracycline can be added to the medium during incubation. Where the transformant transformed by the expression vector using an inducible promoter as the promoter is cultured, an inducer may also be added to the medium, if necessary. For example, when the transformant transformed by an expression vector using a lac promoter is cultured, isopropyl-β-D-thiogalactopyranoside (IPTG), etc. may be added to the medium and indoleacrylic acid (IAA), etc. may be added to the medium in culturing the transformant transformed by an expression vector using a trp promoter.

When the host is bacteria of the genus *Escherichia*, incubation is performed generally at approximately 15 to 43° C. for approximately 3 to 24 hours. If necessary, aeration and agitation may be applied. When the host is bacteria of the genus *Bacillus*, incubation is performed generally at approximately 30 to 40° C. for approximately 6 to 24 hours. If necessary, aeration and agitation may be applied.

Media for incubation of the transformant when the host is yeast include Burkholder's minimal medium (Proc. Natl. Acad. Sci. USA, 77, 4505 (1980)) and an SD medium containing 0.5% (w/v) Casamino acids (Proc. Natl. Acad. Sci. USA, 81, 5330 (1984)). Preferably, the pH of the medium is adjusted to approximately 5 to 8. Incubation is performed generally at approximately 20 to 35° C. for approximately 24 to 72 hours. If necessary, aeration and agitation may be applied.

Media for culturing the transformant when the host is an animal cell include MEM medium supplemented with approximately 5 to 20% (v/v) fetal calf serum (Science, 122, 501 (1952)), DMEM medium (Virology, 8, 396 (1959)), etc. Preferably, the pH of the medium is adjusted to approximately 6 to 8. Incubation is performed generally at approximately 30 to 40° C. for approximately 15 to 60 hours. If necessary, aeration and agitation may be applied.

Media for culturing the transformant when the host is an insect cell include Grace's insect medium (Nature, 195, 788 (1962)) to which additives such as 10% (v/v) immobilized bovine serum are suitably added. Preferably, the pH of the medium is adjusted to approximately 6.2 to 6.4. Incubation is performed generally at approximately 27° C. for approximately 3 to 5 days. If necessary, aeration and agitation may be applied.

Temperatures for incubation at which the transformant transformed by the expression vector comprising the low-temperature expression-inducible promoter sequence and temperatures for expression induction are as described above.

Separation/Purification of Luciferase Mutant of the Invention

The luciferase mutant of the invention can be obtained by separating/purifying the luciferase mutant of the invention from the culture described above. As used herein, the culture is intended to mean any one of a culture broth, cultured cells or cultured bacteria and a cell lysate of the cultured cells or cultured bacteria. The luciferase mutant of the invention can be separated/purified in a conventional manner.

Specifically, when the luciferase mutant of the invention accumulates in the cultured bacteria or cultured cells, after completion of the incubation the bacteria or cells are disrupted in a conventional manner (e.g., ultrasonication, lysozyme, freezing and thawing, etc,) and then a crude extract of the luciferase mutant of the invention can be obtained in a conventional manner (e.g., centrifugation, filtration, etc.). When the luciferase mutant of the invention accumulates in the periplasmic space, after completion of the incubation the extract containing the luciferase mutant of the invention can be obtained in a conventional manner (e.g., the osmotic shock method, etc.). When the luciferase mutant of the invention accumulates in the culture broth, after completion of the incubation the culture supernatant containing the luciferase mutant of the invention can be obtained by separating the bacteria or cells and the culture supernatant in a conventional manner (e.g., centrifugation, filtration, etc.).

The luciferase mutant of the invention contained in the extract or culture supernatant thus obtained can be purified by conventional methods of separation and purification. Examples of these methods for separation and purification which may be used include ammonium sulfate precipitation, gel filtration chromatography, ion-exchange chromatography, affinity chromatography, reversed-phase high-performance liquid chromatography, dialysis, ultrafiltration, etc., alone or in a suitable combination thereof. When the luciferase mutant of the invention contains the peptide sequence for purification described above, it is preferred to perform purification using the same. Specifically, when the luciferase mutant of the invention contains a histidine tag sequence, nickel chelate affinity chromatography may be used; when the luciferase mutant of the invention contains the binding domain of S-transferase to glutathione, affinity chromatography with a glutathione-binding gel may be used; when the luciferase mutant of the invention contains the amino acid sequence of Protein A, antibody affinity chromatography may be used.

5. Use of Luciferase Mutant of the Invention

Use as Detection Marker by Luminescence

The luciferase mutant of the invention can be utilized as a detection marker ("detection marker for the invention") which emits luminescence in the presence of a luciferin. The detection marker of the invention can be utilized for detection of the target substance in, e.g., an immunoassay, a hybridization assay, etc.

The luciferase mutant of the invention can be expressed, e.g., as a fusion protein with a target protein, and introduced into cells by means of the microinjection method, etc., and the resulting product can be used to determine distribution of the target protein described above. The distribution of such a target protein or the like can be determined by using detection methods such as luminescence imaging. In addition to the introduction into cells by means of the microinjection method or the like, the luciferase mutant of the invention can be expressed in cells to provide for use.

The luminescence substrate (luciferin) used is preferably coelenterazines, and particularly preferably, coelenterazine, as described above.

Use as Reporter Protein

The luciferase mutant of the invention may also be used as a reporter protein to assay the transcription activity of promoters, etc. In this case, the polynucleotide of the invention is used as a reporter gene and the luciferase mutant encoded by the reporter gene is contacted with luciferin. As used herein, the term "contact" is intended to mean that the luciferase mutant of the invention and a luciferin are allowed to be present in the same reaction system or culture system, which includes, for example, addition of a luciferin to a culture container charged with cells expressing the luciferase mutant of the invention, mixing the cells with a luciferin and incubation of the cells in the presence of luciferin. The polynucleotide encoding the luciferase mutant of the invention (i.e., the polynucleotide of the invention) is fused to a target promoter or some other expression control sequence (e.g., an enhancer, etc.) to construct a vector. By introducing the vector into a host cell and detecting the luminescence from the luciferase mutant of the invention in the presence of a luciferin (luminescence substrate), the activity of the target promoter or some other expression control sequence can be assayed. Furthermore, the expressed luciferase mutant is reacted with coelenterazines and the luminescence generated may also be visualized in pictures by using a high-sensitive detector.

The luciferin used is preferably coelenterazines, and particularly preferably, coelenterazine, as described above.

The cells used are preferably animal cells. In the case of animal cells, the luciferase mutant in a preferred embodiment of the invention is hardly secreted outside the cells.

The polynucleotide of the invention can be used as a reporter gene in such a manner as described above.

Material for Amusement Supplies

The luciferase mutant of the invention has the activity of catalyzing the reaction where a luciferin is oxidized with oxygen molecules to form oxyluciferin in its excited state. The oxyluciferin in the excited state emits visible light to decay to the ground state. Accordingly, the luciferase mutant of the invention can be used preferably as a luminescent material for amusement supplies. Examples of such amusement supplies are luminescent soap bubbles, luminescent ice bars, luminescent candies, luminescent color paints, etc. These amusement supplies of the invention can be prepared in a conventional manner.

The luciferin used is preferably coelenterazines, and particularly preferably, coelenterazine, as described above.

Bioluminescence Resonance Energy Transfer (BRET) Method

By utilizing the principle of interaction between molecules by the bioluminescence resonance energy transfer (BRET) method, the luciferase mutant of the invention is available for analytical methods such as analysis of physiological functions, assay of enzyme activities, etc.

For instance, when the luciferase mutant of the invention is used as a donor and the fluorescent substance (e.g., an organic compound, a fluorescent protein, etc.) is used as an acceptor, the interactions between the donor and acceptor above can be detected by inducing bioluminescence resonance energy transfer (BRET) between them.

In an embodiment of the present invention, the organic compound used as an acceptor includes Hoechist3342, Indo-1, DAP1, etc. In another embodiment of the present invention, the fluorescent protein used as an acceptor includes a green fluorescent protein (GFP), a blue fluorescent protein (BFP), a muted GFP fluorescent protein, phycobilin, etc.

In a preferred embodiment of the present invention, the physiological functions to be analyzed include an orphan receptor (especially, a G protein-coupled receptor), apoptosis, transcription regulation by gene expression, etc. In a further preferred embodiment of the present invention, the enzyme to be analyzed is protease, esterase, kinase, or the like.

Analysis of the physiological functions by the BRET method can be performed by known methods, for example, by modifications of the method described in Biochem. J. 2005, 385, 625-637 or Expert Opin. Ther Tarets, 2007 11: 541-556. Enzyme activities may also be assayed by known methods, for example, by modifications of the method described in Nature Methods 2006, 3:165-174 or Biotechnol. J. 2008, 3:311-324.

The luminescence substrate (luciferin) used is preferably coelenterazines, and particularly preferably, coelenterazine, as described above.

6. Kit of the Invention

The present invention also provides a kit comprising any one selected from the luciferase mutant of the invention, the polynucleotide of the invention, the recombinant vector of the invention and the transformant of the invention. The kit of the invention may further contain a luciferin.

The luciferin is preferably coelenterazines, and particularly preferably, coelenterazine, as described above.

The kit of the present invention may be prepared with conventional materials by conventional methods. The kit of the present invention may further contain, e.g., sample tubes, plates, instructions for the kit user, solutions, buffers, reagents, and samples suitable for standardization or control samples. The kit of the present invention may further contain salts including halide ions.

The kit of the present invention can be used for the measurement using the reporter protein or reporter gene described above, the analysis of physiological functions by the BRET method, the measurement of enzyme activities, and the like. The kit of the present invention can be used for the method for luminescence reaction as described below.

7. Method for Luminescence Reaction

Luminescence Activity

The luciferase mutant of the invention has the ability of catalyzing the reaction which involves oxidization of a luciferin with oxygen molecules to form an oxyluciferin in its excited state. The oxyluciferin in the excited state emits light on returning to the ground state. That is, the luciferase mutant of the invention catalyzes the luminescence reaction in which a luciferin serves as a substrate to cause luminescence. This activity is sometimes referred to as the "luminescence activity" herein.

Luminescence Reaction

The luminescence reaction using the luciferase mutant of the invention in which a luciferin serves as a substrate can be performed by contacting the luciferase mutant of the invention with the luciferin. As used herein, the term "contact" is intended to mean that the luciferase mutant of the invention and a luciferin are allowed to be present in the same reaction system, which includes, for example, addition of the luciferase mutant of the invention to a container charged with a luciferin, addition of a luciferin to a container charged with the luciferase mutant of the invention and mixing the luciferase mutant of the invention with a luciferin. The reaction can be carried out under conditions conventionally used for the luminescence reaction using *Oplophorus* luciferase or under conditions modified therefrom.

Specifically, solvents for the reaction which are employed are, for example, a buffer solution such as Tris-HCl buffer, sodium phosphate buffer, etc., water, and the like.

Temperatures for the reaction are generally at approximately 4° C. to 40° C. and preferably approximately 4° C. to 25° C.

In the reaction solution, pH is generally approximately 5 to 10, preferably approximately 6 to 9, more preferably approximately 7 to 8 and most preferably approximately 7.5.

The luciferin is preferably coelenterazines, and particularly preferably, coelenterazine, as described above.

The luciferin may also be added to the reaction system in the form of a solution in a polar solvent such as dimethylformamide, dimethylsulfoxide, etc., or in an alcohol such as methanol, ethanol, butanol, etc.

Activation of Luminescence Activity

The luminescence activity of the luciferase mutant of the invention is activated by halide ions, nonionic surfactants, etc.

Examples of the halide ions are fluorine ions, chlorine ions, bromine ions and iodine ions; preferred are chlorine ions, bromine ions and iodine ions.

The concentration of the halide ions is generally approximately 10 µM to 100 mM, preferably approximately 100 µM to 50 mM and particularly preferably approximately 1 mM to 20 mM.

The addition of the halide ions to the reaction system is performed by a method which comprises adding them in a salt form. The salts used are alkali metal salts such as sodium salts, potassium salts, etc.; alkaline earth metal salts such as calcium salts, magnesium salts, barium salts, etc. More specific examples are NaF, NaCl, NaBr, NaI, KF, KCl, KBr, KI, $CaF_2$, $CaCl_2$, $CaBr_2$, $CaI_2$, $MgF_2$, $MgCl_2$, $MgBr_2$, $MgI_2$, etc.

Examples of nonionic surfactants which are commercially available (trade name) include Tween 20 (polyoxyethylene sorbitan monolaurate), Tween 80 (polyoxyethylene sorbitan monooleate), Triton X-100 (polyethylene glycol-p-isooctyl-phenyl ether), Briji-58 (polyoxyethylene (20) cetyl ether), Nonidet P-40 (ethylphenolpoly(ethylene glycol ether)n), etc., and preferably, Tween 20, Triton X-100, etc.

Concentration of the nonionic surfactant is generally approximately 0.0002% (w/v) to 0.2% (w/v), preferably, approximately 0.001% (w/v) to 0.1% (w/v), and particularly preferably, approximately 0.05% (w/v) to 0.02% (w/v).

Regardless of their purposes, all of the documents and publications described in the specification are incorporated herein by reference, each in its respective entirety.

Unless otherwise indicated with respect to the embodiments and working examples, the methods described in standard sets of protocols such as J. Sambrook, E. F. Fritsch & T. Maniatis (Ed.), Molecular cloning, a laboratory manual (4th edition), Cold Spring Harbor Press, Cold Spring Harbor, N.Y. (2012); F. M. Ausubel, R. Brent, R. E. Kingston, D. D. Moore, J. G. Seidman, J. A. Smith, K. Struhl (Ed.), Current Protocols in Molecular Biology, John Wiley & Sons Ltd., etc. or modifications or variations thereof are used. When commercially available reagent kits or measuring apparatuses are used, protocols attached to them are used unless otherwise indicated.

The objects, characteristics and advantages of the present invention as well as the idea thereof are apparent to those skilled in the art from the descriptions given herein. Based on the description given herein, those skilled in the art can easily reproduce the present invention.

It can be understood that the embodiments of the invention, specific working examples, etc. are disclosed as preferred embodiments of the present invention. These descriptions are only for illustrative and explanatory purposes and are not intended to restrict the invention thereto. It is further apparent to those skilled in the art that various modifications may be made based on the descriptions given herein within the intent and scope of the present invention disclosed herein.

EXAMPLES

Hereinafter, the present invention will be described with reference to specific examples but is not deemed to be limited thereto.

Example 1

Preparation of Mutated 19kOLase Gene

Amino acid substitutions by site-specific mutagenesis on the gene for 19kOLase (hereinafter designated as KAZ) were performed by PCR in accordance with the method described in Ho et al., Gene (1989) 77: 51-59. The nucleotide sequence and amino acid sequence of KAZ are shown in SEQ ID NO: 1 and SEQ ID NO: 2, respectively. Specifically, PCR (cycle conditions: 25 cycles of 1 min/94° C., 1 min/50° C., 1 min/72° C.) was performed using pCold-KAZ or pCold-ZZ-KAZ carrying the KAZ gene as a temperate with two PCR primers on a PCR kit (manufactured by Takara Bio Inc.).

For example, the gene for single amino acid substitution mutant KAZ-Q18L was produced as follows. First, DNA fragments amplified by the primers were prepared using pCold-KAZ as a template.

Primer used to prepare the first DNA fragment:

```
pCold-F
                                        (SEQ ID NO: 17)
(5' ACG CCA TAT CGC CGA AAG G 3')

KAZ: Q18L-R
                                        (SEQ ID NO: 18)
(5' TAA CAC TTG ATC TAG GTT GTA TCC AGC 3')
```

Primer used to prepare the second DNA fragment:

```
KAZ: Q18L-F
                                        (SEQ ID NO: 19)
(5' GCT GGA TAC AAC CTA GAT CAA GTG TTA 3')

KAZ-5C/XbaI
                                        (SEQ ID NO: 20)
(5' CCGC TCT AGA TTA GGC AAG AAT GTT CTC GCA
AAG CCT 3')
```

The two DNA fragments prepared above were amplified by a second PCR using the PCR primers KAZ-8N/EcoRI and KAZ-5C/XbaI as below.

Primers:

KAZ-8N/EcoRI
(SEQ ID NO: 21)
(5' GCG AAT TCT TTT ACG TTG GCA GAT TTC GTT GGA 3')

KAZ-5C/XbaI
(SEQ ID NO: 20)

The results indicate that the KAZ gene region (KAZ-Q18L) wherein the amino acid of glutamine at the position of 18 was substituted by leucine in the amino acid sequence of SEQ ID NO: 2 was amplified.

Amino acid substitution was performed in the same manner as described above, using the templates and primers listed in TABLE 1 to acquire the amino acid substituted KAZ gene regions.

TABLE 1

List of templates and PCR primers used for single amino acid substitution of KAZ proteins

| Substitution position | | Template | | Primer | Sequence |
|---|---|---|---|---|---|
| A4E | PCR | pCold-ZZ-KAZ | a | KAZ: A4E-F | 5' ccg gaa ttc TTT ACG CTG GAG GAT TTC GTT GGA GAC 3' (SEQ ID NO: 22) |
| | | | b | KAZ-5C/XbaI | 5' ccgc TCT AGA TTA GGC AAG AAT GTT CTC GCA AAG CCT 3' (SEQ ID NO: 20) |
| Q11R | PCR | pCold-ZZ-KAZ | a | KAZ: Q11R-F | 5' ccggaattcTTTACGTTGGCAGATTTCGTTGGAGA CTGGCGACAGACAGCTGG 3' (SEQ ID NO: 23) |
| | | | b | KAZ-5C/XbaI | 5' ccgc TCT AGA TTA GGC AAG AAT GTT CTC GCA AAG CCT 3' (SEQ ID NO: 20) |
| Q18L | 1st PCR | pCold-KAZ | a | pCold-F | 5' ACG CCA TAT CGC CGA AAG G 3' (SEQ ID NO: 17) |
| | | | b | KAZ: Q18L-R | 5' TAA CAC TTG ATC TAG GTT GTA TCC AGC 3' (SEQ ID NO: 18) |
| | | pCold-KAZ | c | KAZ: Q18L-F | 5' GCT GGA TAC AAC CTA GAT CAA GTG TTA 3' (SEQ ID NO: 19) |
| | | | d | KAZ-5C/XbaI | 5' ccgc TCT AGA TTA GGC AAG AAT GTT CTC GCA AAG CCT 3' (SEQ ID NO: 20) |
| | 2nd PCR | 1st PCR product | a | KAZ-8N/EcoRI | 5' gcg AAT TCT TTT ACG TTG GCA GAT TTC GTT GGA 3' (SEQ ID NO: 21) |
| | | | d | KAZ-5C/XbaI | 5' ccgc TCT AGA TTA GGC AAG AAT GTT CTC GCA AAG CCT 3' (SEQ ID NO: 20) |
| L27V | 1st PCR | pCold-KAZ | a | pCold-F | 5' ACG CCA TAT CGC CGA AAG G 3' (SEQ ID NO: 17) |
| | | | b | KAZ: L27V-R | 5' GAA CAG ACT AGA CAC TCC TCC TTG TTC 3' (SEQ ID NO: 24) |
| | | pCold-KAZ | c | KAZ: L27V-F | 5' GAA CAA GGA GGA GTG TCT AGT CTG TTC 3' (SEQ ID NO: 25) |
| | | | d | KAZ-5C/XbaI | 5' ccgc TCT AGA TTA GGC AAG AAT GTT CTC GCA AAG CCT 3' (SEQ ID NO: 20) |
| | 2nd PCR | 1st PCR product | a | KAZ-8N/EcoRI | 5' gcg AAT TCT TTT ACG TTG GCA GAT TTC GTT GGA 3' (SEQ ID NO: 21) |
| | | | d | KAZ-5C/XbaI | 5' ccgc TCT AGA TTA GGC AAG AAT GTT CTC GCA AAG CCT 3' (SEQ ID NO: 20) |
| A33N | 1st PCR | pCold-ZZ-KAZ | a | KAZ-8N/EcoRI | 5' gcg AAT TCT TTT ACG TTG GCA GAT TTC GTT GGA 3' (SEQ ID NO: 21) |
| | | | b | A33N-R | 5' TGA CAC TCC CAG GTT TTG AAC AG ACT 3' (SEQ ID NO: 26) |
| | | pCold-ZZ-KAZ | c | A33N-F | 5' AGT CTG TTC CAA AAC CTG GGA GTG TCA 3' (SEQ ID NO: 27) |
| | | | d | KAZ-5C/XbaI | 5' ccgc TCT AGA TTA GGC AAG AAT GTT CTC GCA AAG CCT 3' (SEQ ID NO: 20) |
| | 2nd PCR | 1st PCR product | a | KAZ-8N/EcoRI | 5' gcg AAT TCT TTT ACG TTG GCA GAT TTC GTT GGA 3' (SEQ ID NO: 21) |
| | | | d | KAZ-5C/XbaI | 5' ccgc TCT AGA TTA GGC AAG AAT GTT CTC GCA AAG CCT 3' (SEQ ID NO: 20) |
| K43R | 1st PCR | pCold-KAZ | a | KAZ-8N/EcoRI | 5' gcg AAT TCT TTT ACG TTG GCA GAT TTC GTT GGA 3' (SEQ ID NO: 21) |
| | | | b | KAZ: K43R-R | 5' AGA CAG TAC AAC TCT CTG TAT GGG CGT 3' (SEQ ID NO: 28) |
| | | pCold-KAZ | c | KAZ: L43R-F | 5' ACG CCC ATA CAG AGA GTT GTA CTG TCT 3' (SEQ ID NO: 29) |
| | | | d | KAZ-5C/XbaI | 5' ccgc TCT AGA TTA GGC AAG AAT GTT CTC GCA AAG CCT 3' (SEQ ID NO: 20) |

TABLE 1-continued

List of templates and PCR primers
used for single amino acid substitution of KAZ proteins

| Substitution position | | Template | | Primer | Sequence |
|---|---|---|---|---|---|
| | 2nd PCR | 1st PCR product | a | KAZ-8N/EcoRI | 5' gcg AAT TCT TTA CGT TGC AGA TTC GTT GGA 3' (SEQ ID NO: 21) |
| | | | d | KAZ-5C/XbaI | 5' ccgc TCT AGA TTA GGC AAG AAT GTT CTC GCA AAG CCT 3' (SEQ ID NO: 20) |
| V44I | 1st PCR | pCold-ZZ-KAZ | a | KAZ-8N/EcoRI | 5' gcg AAT TCT TTA CGT TGC AGA TTC GTT GGA 3' (SEQ ID NO: 21) |
| | | | b | KAZ: V44I-R | 5' CCC AGA CAG TAC TAT TTT CTG TAT GGG 3' (SEQ ID NO: 30) |
| | | pCold-ZZ-KAZ | c | KAZ: V44I-F | 5' CCC ATA CAG AAA ATA GTA CTG TCT GGG 3' (SEQ ID NO: 31) |
| | | | d | KAZ-5C/XbaI | 5' ccgc TCT AGA TTA GGC AAG AAT GTT CTC GCA AAG CCT 3' (SEQ ID NO: 20) |
| | 2nd PCR | 1st PCR product | a | KAZ-8N/EcoRI | 5' gcg AAT TCT TTA CGT TGC AGA TTC GTT GGA 3' (SEQ ID NO: 21) |
| | | | d | KAZ-5C/XbaI | 5' ccgc TCT AGA TTA GGC AAG AAT GTT CTC GCA AAG CCT 3' (SEQ ID NO: 20) |
| A54I | 1st PCR | pCold-ZZ-KAZ | a | KAZ-8N/EcoRI | 5' gcg AAT TCT TTA CGT TGC AGA TTC GTT GGA 3' (SEQ ID NO: 21) |
| | | | b | KAZ: A54I-R | 5' GAC ATG AAT ATC GAT TTT AAC CCA TT 3' (SEQ ID NO: 32) |
| | | pCold-ZZ-KAZ | c | KAZ: A54I-F | 5' AAT GGG TTA AAA ATC GAT ATT CAT GTC 3' (SEQ ID NO: 33) |
| | | | d | pCold-R | 5' TGG CAG GGA TCT AGA ATT CTG 3' (SEQ ID NO: 34) |
| | 2nd PCR | 1st PCR product | a | KAZ-8N/EcoRI | 5' gcg AAT TCT TTA CGT TGC AGA TTC GTT GGA 3' (SEQ ID NO: 21) |
| | | | d | KAZ-5C/XbaI | 5' ccgc TCT AGA TTA GGC AAG AAT GTT CTC GCA AAG CCT 3' (SEQ ID NO: 20) |
| F68D | 1st PCR | pCold-KAZ | a | KAZ-8N/EcoRI | 5' gcg AAT TCT TTA CGT TGC AGA TTC GTT GGA 3' (SEQ ID NO: 21) |
| | | | b | KAZ: F68D-R | 5' TAG ACC CAT TTG ATC ACC ACT GAG TCC 3' (SEQ ID NO: 35) |
| | | pCold-KAZ | c | KAZ: F68D-F | 5' GGA CTC AGT GGT GAT CAA ATG GGT CTA 3' (SEQ ID NO: 36) |
| | | | d | KAZ-5C/XbaI | 5' ccgc TCT AGA TTA GGC AAG AAT GTT CTC GCA AAG CCT 3' (SEQ ID NO: 20) |
| | 2nd PCR | 1st PCR product | a | KAZ-8N/EcoRI | 5' gcg AAT TCT TTA CGT TGC AGA TTC GTT GGA 3' (SEQ ID NO: 21) |
| | | | d | KAZ-5C/XbaI | 5' ccgc TCT AGA TTA GGC AAG AAT GTT CTC GCA AAG CCT 3' (SEQ ID NO: 20) |
| L72Q | 1st PCR | pCold-KAZ | a | KAZ-8N/EcoRI | 5' gcg AAT TCT TTA CGT TGC AGA TTC GTT GGA 3' (SEQ ID NO: 21) |
| | | | b | KAZ: L72Q-R | 5' GAT CAT TTC AAT TTG ACC CAT TTG AAA 3' (SEQ ID NO: 37) |
| | | pCold-KAZ | c | KAZ: L72Q-F | 5' TTT CAA ATG GGT CAA ATT GAA ATG ATC 3' (SEQ ID NO: 38) |
| | | | d | KAZ-5C/XbaI | 5' ccgc TCT AGA TTA GGC AAG AAT GTT CTC GCA AAG CCT 3' (SEQ ID NO: 20) |
| | 2nd PCR | 1st PCR product | a | KAZ-8N/EcoRI | 5' gcg AAT TCT TTA CGT TGC AGA TTC GTT GGA 3' (SEQ ID NO: 21) |
| | | | d | KAZ-5C/XbaI | 5' ccgc TCT AGA TTA GGC AAG AAT GTT CTC GCA AAG CCT 3' (SEQ ID NO: 20) |
| M75K | 1st PCR | pCold-KAZ | a | KAZ-8N/EcoRI | 5' gcg AAT TCT TTA CGT TGC AGA TTC GTT GGA 3' (SEQ ID NO: 21) |
| | | | b | KAZ: M75K-R | 5' AAC TTT GAA GAT CTT TTC AAT TAG ACC 3' (SEQ ID NO: 39) |
| | | pCold-KAZ | c | KAZ: M75K-F | 5' GGT CTA ATT GAA AAG ATC TTC AAA GTT 3' (SEQ ID NO: 40) |
| | | | d | KAZ-5C/XbaI | 5' ccgc TCT AGA TTA GGC AAG AAT GTT CTC GCA AAG CCT 3' (SEQ ID NO: 20) |

TABLE 1-continued

List of templates and PCR primers used for single amino acid substitution of KAZ proteins

| Substitution position | | Template | | Primer | Sequence |
|---|---|---|---|---|---|
| | 2nd PCR | 1st PCR product | a | KAZ-8N/EcoRI | 5' gcg AAA TTC TTT ACG TTG GCA GAT TTC GTT GGA 3' (SEQ ID NO: 21) |
| | | | d | KAZ-5C/XbaI | 5' ccgc TCT AGA TTA GGC AAG AAT GTT CTC GCA AAG CCT 3' (SEQ ID NO: 20) |
| I90V | 1st PCR | pCold-KAZ | a | KAZ-8N/EcoRI | 5' gcg AAA TTC TTT ACG TTG GCA GAT TTC GTT GGA 3' (SEQ ID NO: 21) |
| | | | b | KAZ: I90V-R | 5' ATA ATG GAG AAT AAC CTT GAA ATG ATG 3' (SEQ ID NO: 41) |
| | | pCold-KAZ | c | KAZ: I90V-F | 5' CAT CAT TTC AAG GTT ATT CTC CAT TAT 3' (SEQ ID NO: 42) |
| | | | d | KAZ-5C/XbaI | 5' ccgc TCT AGA TTA GGC AAG AAT GTT CTC GCA AAG CCT 3' (SEQ ID NO: 20) |
| | 2nd PCR | 1st PCR product | a | KAZ-8N/EcoRI | 5' gcg AAA TTC TTT ACG TTG GCA GAT TTC GTT GGA 3' (SEQ ID NO: 21) |
| | | | d | KAZ-5C/XbaI | 5' ccgc TCT AGA TTA GGC AAG AAT GTT CTC GCA AAG CCT 3' (SEQ ID NO: 20) |
| P115E | 1st PCR | pCold-KAZ | a | KAZ-8N/EcoRI | 5' gcg AAA TTC TTT ACG TTG GCA GAT TTC GTT GGA 3' (SEQ ID NO: 21) |
| | | | b | KAZ: P115E-R | 5' TAC AGC AAT TCC TTC GTA AGG TCT TCC 3' (SEQ ID NO: 43) |
| | | pCold-KAZ | c | KAZ: P115E-F | 5' GGA AGA CCT TAC GAA GGA ATT GCT GTA 3' (SEQ ID NO: 44) |
| | | | d | KAZ-5C/XbaI | 5' ccgc TCT AGA TTA GGC AAG AAT GTT CTC GCA AAG CCT 3' (SEQ ID NO: 20) |
| | 2nd PCR | 1st PCR product | a | KAZ-8N/EcoRI | 5' gcg AAA TTC TTT ACG TTG GCA GAT TTC GTT GGA 3' (SEQ ID NO: 21) |
| | | | d | KAZ-5C/XbaI | 5' ccgc TCT AGA TTA GGC AAG AAT GTT CTC GCA AAG CCT 3' (SEQ ID NO: 20) |
| Q124K | 1st PCR | pCold-KAZ | a | KAZ-8N/EcoRI | 5' gcg AAA TTC TTT ACG TTG GCA GAT TTC GTT GGA 3' (SEQ ID NO: 21) |
| | | | b | KAZ: Q124K-R | 5' AGT AAC TGT GAT CTT CTT GCC GTC AAA 3 (SEQ ID NO: 45) |
| | | pCold-KAZ | c | KAZ: Q124K-F | 5' TTT GAC GGC AAG AAG ATC ACA GTT ACT 3' (SEQ ID NO: 46) |
| | | | d | pCold-R | 5' TGG CAG GGA TCT TAG ATT CTG 3' (SEQ ID NO: 34) |
| | 2nd PCR | 1st PCR product | a | KAZ-8N/EcoRI | 5' gcg AAA TTC TTT ACG TTG GCA GAT TTC GTT GGA 3' (SEQ ID NO: 21) |
| | | | d | KAZ-5C/XbaI | 5' ccgc TCT AGA TTA GGC AAG AAT GTT CTC GCA AAG CCT 3' (SEQ ID NO: 20) |
| Y138I | 1st PCR | pCold-ZZ-KAZ | a | KAZ-8N/EcoRI | 5' gcg AAA TTC TTT ACG TTG GCA GAT TTC GTT GGA 3' (SEQ ID NO: 21) |
| | | | b | KAZ: Y138I-R | 5' TAG CCT CTC ATC AAT GAT CTT GTT GCC 3' (SEQ ID NO: 47) |
| | | pCold-ZZ-KAZ | c | KAZ: Y138I-F | 5' GGC AAC AAG ATC ATT GAT GAG AGG CTA 3' (SEQ ID NO: 48) |
| | | | d | pCold-R | 5' TGG CAG GGA TCT TAG ATT CTG 3' (SEQ ID NO: 34) |
| | 2nd PCR | 1st PCR product | a | KAZ-8N/EcoRI | 5' gcg AAA TTC TTT ACG TTG GCA GAT TTC GTT GGA 3' (SEQ ID NO: 21) |
| | | | d | KAZ-5C/XbaI | 5' ccgc TCT AGA TTA GGC AAG AAT GTT CTC GCA AAG CCT 3' (SEQ ID NO: 20) |
| N166R | PCR | pCold-ZZ-KAZ | a | KAZ-8N/EcoRI | 5' gcg AAA TTC TTT ACG TTG GCA GAT TTC GTT GGA 3' (SEQ ID NO: 21) |
| | | | b | KAZ: N166R-R | 5' gcc TCT AGA TTA GGC AAG AAT CCT CTC GCA AAG 3' (SEQ ID NO: 49) |

Example 2

Preparation of Mutated 19kOLase Gene (dnKAZ) with 16 Mutations

Using pCold-ZZ-P-nanoKAZ described in Inouye et al. (2013) Biochem. Biophys. Res. Commun. 437: 23-28, gene amplification was performed by PCR using the following primers.

Primers:

```
nanoKAZ-1N/EcoRI
                                        (SEQ ID NO: 50)
(5' gcgGAATTCTTCACCCTGGAGGACTTCGTCGGC 3':
EcoRI sequence underlined)

nanoKAZ-3C/XbaI
                                        (SEQ ID NO: 51)
(5' gccTCTAGATTAGGCCAGGATTCTCTCGCACAGTCT 3':
XbaI sequence underlined)
```

Example 3

Construction of Expression Vectors for KAZ Mutant Using pCold II Vector in E. coli The DNA fragments obtained in EXAMPLES 1 and 2 were purified on a PCR purification kit (manufactured by Qiagen Inc.), digested with restriction enzymes EcoRI/XbaI in a conventional manner and then ligated to an expression vector pCold II (Takara Bio Inc.) at the restriction enzyme EcoRI/XbaI site to construct the KAZ mutant vectors as follows: pCold-KAZ-A4E, pCold-KAZ-Q11R, pCold-KAZ-Q18L, pCold-KAZ-L27V, pCold-KAZ-A33N, pCold-KAZ-K43R, pCold-KAZ-V44I, pCold-KAZ-A54I, pCold-KAZ-F68D, pCold-KAZ-L72Q, pCold-KAZ-M75K, pCold-KAZ-I90V, pCold-KAZ-P115E, pCold-KAZ-Q124K, pCold-KAZ-Y138I, pCold-KAZ-N166R and pCold-dnKAZ. The nucleotide sequences of the insert DNAs were confirmed by sequencing using a DNA Sequencer (manufactured by ABI Inc.).

In the amino acid sequences of the KAZ mutants, substituted amino acids and nucleotides are shown in TABLE 2.

TABLE 2

| KAZ Mutant (KAZ-) | Nucleotide Sequence | |
|---|---|---|
| | Before Substitution (wild) | After Substitution (mutant) |
| A4E | 10 GCA (A) | 10 GAG (E) |
| Q11R | 31 CAA (Q) | 31 AGA (R) |
| Q18L | 52 CAA (Q) | 52 CTG (L) |
| L27V | 79 TTG (L) | 79 GTC (V) |
| A33N | 33 GCA (A) | 33 AAC (N) |
| K43R | 127 AAA (K) | 127 AGA (R) |
| V44I | 130 GTT (V) | 130 ATC (I) |
| A54I | 160 GCT (A) | 160 ATC (I) |
| F68D | 202 TTT (F) | 202 GAC (D) |
| L72Q | 214 CTA (L) | 214 CAG (Q) |
| M75K | 223 ATG (M) | 223 AAG (K) |
| I90V | 268 ATT (I) | 268 GTC (V) |
| P115E | 343 CCT (P) | 343 GAG (E) |
| Q124K | 370 CAG (Q) | 370 AAG (K) |
| Y138I | 412 TAT (Y) | 412 ATC (I) |
| N166R | 496 AAC (N) | 496 AGA (R) |

In the KAZ mutants, the nucleotide sequence and amino acid sequence of KAZ-V44I are shown in SEQ ID NO: 3 and SEQ ID NO: 4, respectively. The nucleotide sequence and amino acid sequence of KAZ-A54I are shown in SEQ ID NO: 5 and SEQ ID NO: 6, respectively. The nucleotide sequence and amino acid sequence of KAZ-Y138I are shown in SEQ ID NO: 7 and SEQ ID NO: 8, respectively.

Example 4

Expression of KAZ Mutants in E. coli and Preparation of Crude Enzyme Solution In order to express the KAZ mutants in E. coli, the recombinant plasmid prepared in EXAMPLE 3 was used. The E. coli BL21 strain (Novagen, Madison, Wis.) was used as a host cell. The BL21 strain carrying the recombinant plasmid was incubated in 5 mL of Luria-Bertani medium (hereinafter designated as LB medium) containing ampicillin (50 µg/mL) at 37° C. for 18 hours. This seed culture, 0.1 mL, was inoculated to 10 mL of LB medium and incubated for 3 hours, followed by cooling in an ice-water bath for 1 hour. IPTG was added to the culture medium at a final concentration of 1 mM, followed by incubation at 15° C. for further 20 hours. After completion of the incubation, 1 mL of the cultured medium was harvested by centrifugation at 10,000 rpm for 2 minutes. The thus collected E. coli cells were suspended in 0.5 mL of 30 mM Tris-HCl (pH 7.6)-10 mM EDTA (manufactured by Wako Pure Chemical Industries, Ltd.) (hereinafter designated as TE). The E. coli cells were disrupted by sonication for 3 seconds using a Branson Model 250 Sonifier (Danbury, Conn.) to give a crude enzyme solution. After 0.5 mL of the crude enzyme solution was further centrifuged at 10,000 rpm for 2 minutes to separate the supernatant from the precipitate, the precipitate was suspended in 0.5 mL of TE. Then 20 µL each of the supernatant and precipitate were analyzed by SDS-PAGE to confirm the presence or absence of soluble and insoluble proteins. The results are shown in FIG. 1, wherein M and 1 to 17 denote: M: molecular weight size markers; 1: KAZ; 2 KAZ-A4E; 3: KAZ-Q11R; 4: KAZ-Q18L; 5: KAZ-L27V; 6: KAZ-A33N; 7: KAZ-K43R; 8: KAZ-V44I; 9: KAZ-A54I; 10: KAZ-F68D; 11: KAZ-L72Q; 12: KAZ-M75K; 13: KAZ-I90V; 14: KAZ-P115E; 15: KAZ-Q124K; 16: KAZ-Y138I; 17: KAZ-N166R and 18: dnKAZ. It is clearly observed from FIG. 1 that only dnKAZ (18) was expressed as a soluble protein and the other proteins (1 to 16) were expressed mostly as insoluble proteins.

Example 5

Assay for Luminescence Activity of KAZ Mutants in Crude Enzyme Solution

A luminescence reaction was started by the addition of 5 µL each of the supernatant and precipitate obtained in EXAMPLE 4 to 100 µL of TE containing 0.5 µg of coelenterazine (manufactured by JNC Corp.). The luminescence activity was measured for 60 seconds using a luminometer (manufactured by Atto Corp.: AB2200) and expressed in terms of relative luminescence activity ($I_{max}$).

TABLE 3. Luminescence activities of the supernatant and precipitate fractions in KAZ mutants in crude enzyme solutions

TABLE 3

| Expression Vector (pCold-) | Relative Luminescence Activity ($I_{max}$) | |
|---|---|---|
| | Supernatant | Precipitate |
| KAZ | 1.0 | 0.1 |
| KAZ-A4E | 1.5 | 0.2 |
| KAZ-Q11R | 2.0 | 0.3 |
| KAZ-Q18L | 1.0 | 0.2 |
| KAZ-L27V | 0.1 | 0.1 |
| KAZ-A33N | 1.0 | 0.4 |
| KAZ-K43R | 1.8 | 0.2 |
| KAZ-V44I | 6.5 | 0.6 |
| KAZ-A54I | 150 | 13 |
| KAZ-F68D | 5.4 | 0.2 |
| KAZ-L72Q | 7.2 | 0.6 |
| KAZ-M75K | 4.6 | 0.4 |
| KAZ-I90V | 2.1 | 0.4 |
| KAZ-P115E | 16 | 1.1 |
| KAZ-Q124K | 7.4 | 0.8 |
| KAZ-Y138I | 32 | 1.4 |
| KAZ-N166R | 4.7 | 0.8 |
| dnKAZ | 1,806 | 10 | dnKAZ was expressed as a soluble protein and showed high luminescence activity in the supernatant. On the other hand, the KAZ mutants were almost all expressed as insoluble proteins and the luminescence activity was low in the supernatant and precipitate fractions. Among others, the KAZ-A54I mutant exhibited the activity of approximately 1/12 times that of dnKAZ; the luminescence activity was enhanced by substituting alanine at the position of 54 with isoleucine.

Example 6

Construction of Expression Vectors for ZZ-Fused KAZ Mutants in *E. Coli*

To express KAZ mutants as soluble proteins, the expression vector of pCold-ZZ-X (described in Inouye & Sahara, Protein Express. Purif. (2009) 66: 52-57) was used. The DNA fragments obtained in EXAMPLES 1 and 2 were digested with restriction enzyme EcoRI/XbaI and ligated to the restriction enzyme EcoRI/XbaI site of this expression vector to construct the following expression vectors for the fused KAZ mutants: pCold-ZZ-P-KAZ-A4E, pCold-ZZ-P-KAZ-Q11R, pCold-ZZ-P-KAZ-Q18L, pCold-ZZ-P-KAZ-L27V, pCold-ZZ-P-KAZ-A33N, pCold-ZZ-P-KAZ-K43R, pCold-ZZ-P-KAZ-V44I, pCold-ZZ-P-KAZ-A54I, pCold-ZZ-P-KAZ-F68D, pCold-ZZ-P-KAZ-L72Q, pCold-ZZ-P-KAZ-M75K, pCold-ZZ-P-KAZ-I90V, pCold-ZZ-P-KAZ-P115E, pCold-ZZ-P-KAZ-Q124K, pCold-ZZ-P-KAZ-Y138I, pCold-ZZ-P-KAZ-N166R, and pCold-ZZ-P-dnKAZ.

Example 7

Figure 2:
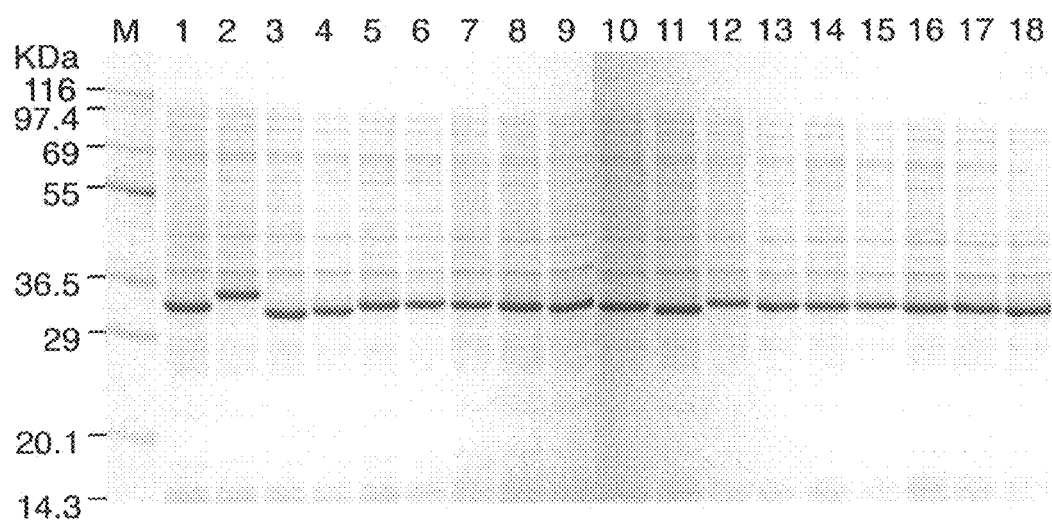
FIG. 2 shows the results of SDS-PAGE analysis of the crude enzyme solution of *E. coli* in which the KAZ mutants were expressed using pCold-ZZ-P vector.

Expression of ZZ-Fused KAZ Mutants in *E. coli* and Preparation of Crude Enzyme Solution To express the ZZ-fused KAZ mutants in *E. coli*, the recombinant plasmid prepared in EXAMPLE 6 was used. Crude enzyme solutions were prepared in the same manner as EXAMPLE 4 using the *E. coli* BL21 strain (Novagen, Madison, Wis.) as a host cell. The resultant crude enzyme solution, 5 μL, was subjected to SDS-PAGE analysis to confirm expression of the proteins (FIG. 2). In FIG. 2, M and 1 to 18 are the same as described in FIG. 1.

Example 8

Assay for Luminescence Activity of ZZ-Fused KAZ Mutants in Crude Enzyme Solutions DTT was added to the crude enzyme solution obtained in EXAMPLE 7 at a final concentration of 1 mM and the mixture was allowed to stand in an ice water for more than 5 hours. A luminescence reaction was started by adding 1 μL of the crude enzyme solution to 100 μL of TE containing 1 μg of coelenterazine (manufactured by JNC Corp.). The luminescence activity was determined using a luminometer (manufactured by Atto Inc.: AB2200) for 60 seconds, and the maximum intensity of luminescence ($I_{max}$) was shown as relative luminescence activity.

The results are shown in TABLE 4. It was confirmed by the results of TABLE 4 that the activities of three mutants of KAZ-V44I, KAZ-A54I and KAZ-Y138I were stimulated by 6.6, 8.9 and 5.9 times higher than that of wild KAZ, respectively. In particular, KAZ-A54I with a single mutation exhibited the luminescence activity comparable to dnKAZ with 16 amino acid mutations, suggesting that the three substitutions may be critical for luminescence enhancement.

TABLE 4. Luminescence activities of ZZ-fused KAZ mutants in crude enzyme solutions

TABLE 4

| Expression Vector (pCold-ZZ-P-) | Relative Luminescence Activity ($I_{max}$) |
|---|---|
| KAZ | 1.0 |
| KAZ-A4E | 0.5 |
| KAZ-Q11R | 1.8 |
| KAZ-Q18L | 0.3 |
| KAZ-L27V | 0.1 |
| KAZ-A33N | 1.0 |
| KAZ-K43R | 0.6 |
| KAZ-V44I | 6.6 |
| KAZ-A54I | 8.9 |
| KAZ-F68D | 2.7 |
| KAZ-L72Q | 2.5 |
| KAZ-M75K | 1.3 |
| KAZ-I90V | 1.8 |
| KAZ-P115E | 4.5 |
| KAZ-Q124K | 3.7 |
| KAZ-Y138I | 5.9 |
| KAZ-N166R | 3.6 |
| dnKAZ | 9.4 |

Example 9

Secretory Expression Vectors for KAZ Mutants Using a Signal Peptide Sequence of *Gaussia* Luciferase for Secretion Expression vectors for the KAZ mutants were constructed as follows. First, a novel expression vector pcDNA3-GLsp for animal culture cells was constructed. Specifically, a signal peptide sequence of *Gaussia* luciferase for secretion was obtained from the pcDNA3-GLuc vector (manufactured by Prolume Ltd.) by PCR using the following primers.

Primers:

```
GLsp-1R/EcoRI
                                        (SEQ ID NO: 52)
(5' ggc GAA TTC GGT GGG CTT GGC CTC GGC CAC 3',
EcoRI sequence underlined)

T7 Primer
                                        (SEQ ID NO: 53)
(5' TAATACG ACTCACTATAGGG 3')
```

The resulting fragment of the signal peptide sequence for secretion was digested with HindIII/EcoRI and inserted into the restriction enzyme HindIII/EcoRI site of pcDNA3 vector (manufactured by Invitrogen Inc.) to construct a novel expression vector pcDNA3-GLsp. The novel expression vector is regulated by CMV promoter, followed by the Kozak sequence, the signal peptide sequence of *Gaussia* luciferase for secretion and a multiple-cloning site sequence.

Next, expression vectors for the KAZ mutants were constructed using the novel expression vector of pcDNA3-GLsp as follows. The KAZ mutant gene fragment was digested with restriction enzymes EcoRI/XbaI in a conventional manner and then ligated to the EcoRI-XbaI site of pcDNA3-GLsp to construct the following expression vectors: pcDNA3-GLsp-KAZ-A4E, pcDNA3-GLsp-KAZ-Q11R, pcDNA3-GLsp-KAZ-Q18L, pcDNA3-GLsp-KAZ-L27V, pcDNA3-GLsp-KAZ-A33N, pcDNA3-GLsp-KAZ-K43R, pcDNA3-GLsp-KAZ-V44I, pcDNA3-GLsp-KAZ-A54I, pcDNA3-GLsp-KAZ-F68D, pcDNA3-GLsp-KAZ-L72Q, pcDNA3-GLsp-KAZ-M75K, pcDNA3-GLsp-KAZ-I90V, pcDNA3-GLsp-KAZ-P115E, pcDNA3-GLsp-KAZ-Q124K, pcDNA3-GLsp-KAZ-Y138I, pcDNA3-GLsp-KAZ-N166R and pcDNA3-GLsp-dnKAZ. The inserted gene sequences were confirmed by sequencing using a DNA Sequencer (manufactured by ABI Inc.).

Example 10

Transfection of Vectors in Animal Culture Cells and Preparation of Enzyme for Assay (1) Purification of Expression Plasmid The following experiment was conducted using the recombinant plasmid obtained in EXAMPLE 9. The recombinant plasmid was purified from the *E. coli* JM83 strain using a plasmid purification kit (manufactured by QIAGEN) and dissolved in sterilized water. Firefly luciferase vector (pGL4.13 [Luc2/sv40]: manufactured by Promega Corp.) was similarly treated and used as an internal standard.

(2) Transfection and Preparation of Enzyme for Assay

Chinese hamster ovary cell line CHO-K1 was cultured in Ham's F-12 medium (manufactured by Wako Pure Chemical Industries, Ltd.) supplemented with 10% (v/v) fetal bovine serum (manufactured by Biowest Inc.). The CHO-K1 cells were plated in a 6-well plate in $1 \times 10^5$ cells/well/2 mL medium (n=2) and cultured in an incubator at 37° C. in 5% (v/v) $CO_2$. After 24 hours, the purified recombinant plasmid was transfected to CHO-K1 cells using a FuGene HD transfection kit (manufactured by Promega Corp.), which was provided for subsequent experiment. Specifically, 1 μg of the recombinant plasmid pGL4.13 [Luc2/sv40], 0.1 μg of the internal standard vector and 3 μL of FuGene HD were added to 100 μL of the medium, which was allowed to stand at room temperature for 15 minutes. Subsequently, 100 μL of the DNA-FuGene complex was added to the cells in the 6 wells. After incubation for 48 hours, the culture medium was collected. On the other hand, the KAZ mutants expressed in the cells were washed 3 times with 3 mL of 1×PBS, then suspended in 1 mL of 1×PBS and disrupted on ice by ultrasonication, which was used as enzyme solutions of the cell-extracts of KAZ mutants.

Example 11

Measurement of Luminescence Activity of KAZ Mutants Expressed in Animal Culture Cells A luminescence reaction was started by adding 5 μL of the culture media and cell extracts obtained in EXAMPLE 10 to 1004 of 30 mM Tris-HCl (pH 7.6)-10 mM EDTA (manufactured by Wako Pure Chemical Industries, Ltd.) containing 0.5 μg of coelenterazine (manufactured by JNC Corp.). The luminescence activity was determined using a luminometer (manufactured by Atto Inc.: AB2200) for 60 seconds, and the maximum intensity of luminescence ($I_{max}$) was defined as a percentage. The results are shown in TABLE 5. In the results of TABLE 5, no secretion from the cells was observed in any of the KAZ mutants with single amino acid substitution.

In firefly luciferase which was used as the internal standard to confirm the efficiency of transfection, 5 μL of the cell extract obtained in EXAMPLE 10 was added to 100 μL of a reagent for enzyme assay (Promega Corp.) to start a luminescence reaction. The luminescence activity was determined as the maximum intensity of luminescence in terms of relative light unit (flu) for 10 seconds using a luminometer (manufactured by Atto Inc.: AB2200). It was confirmed that the transfection efficiencies were almost the same.

TABLE 5. Luminescence Activities of KAZ Mutants Expressed in Animal Culture Cells

TABLE 5

| Expression Vector | Relative Luminescence Activity ($I_{max}$) (%) | |
|---|---|---|
| (pcDNA3-GLsp-) | Culture Medium | Cell Extracts |
| KAZ | less than 0.01 | 0.1 |
| KAZ-A4E | less than 0.01 | 0.1 |
| KAZ-Q11R | less than 0.01 | 0.1 |
| KAZ-Q18L | less than 0.01 | 0.02 |
| KAZ-L27V | less than 0.01 | 0.02 |
| KAZ-A33N | less than 0.01 | 0.1 |
| KAZ-K43R | less than 0.01 | 0.1 |
| KAZ-V44I | less than 0.01 | 0.7 |
| KAZ-A54I | less than 0.01 | 2.4 |
| KAZ-F68D | less than 0.01 | 0.3 |
| KAZ-L72Q | less than 0.01 | 0.4 |
| KAZ-M75K | less than 0.01 | 0.2 |
| KAZ-I90V | less than 0.01 | 0.3 |
| KAZ-P115E | less than 0.01 | 0.3 |
| KAZ-Q124K | less than 0.01 | 0.3 |
| KAZ-Y138I | less than 0.01 | 1.0 |
| KAZ-N166R | less than 0.01 | 0.2 |
| nanoKAZ | 100 | 6.5 |

Example 12

Construction of Genes for the KAZ Mutants with Two Amino Acid Substitutions and Three Amino Acid Substitutions Based on the results in EXAMPLE 8 that three amino acid substitutions (V44I, A54I, Y138I) may be critical for luminescence enhancement, the mutants with these two amino acid substitutions and three amino acid substitutions were constructed to examine the luminescence activity.

The genes for KAZ mutants with two amino acid substitutions and three amino acid substitutions were obtained in the same manner as EXAMPLE 1 using the single amino acid substituted KAZ mutant prepared in EXAMPLE 5 as a template and the PCR primers described in TABLE 6.

By the methods as described above, the mutated regions of KAZ gene for three mutants with two amino acid substitutions (KAZ-V44I-A54I, KAZ-V44I-Y138I and KAZ-A54I-Y138I) and one mutant with three amino acid substitutions (KAZ-V44I-A54I-Y138I) were obtained.

TABLE 6

List of templates and PCR primers used for KAZ proteins with two and three amino acid substitutions

| Substitution position | | Template | | Primer | Sequence |
|---|---|---|---|---|---|
| V44I-A54I | 1st PCR | pCold-ZZ-P-V44I-KAZ | a | KAZ-8N/EcoRI | 5' gcg AAA TTC TTT ACG TTG GCA GAT TTC GTT GGA 3' (SEQ ID NO: 21) |
| | | | b | KAZ: A54I-R | 5' GAC ATG AAT ATC GAT TTT TAA CCC ATT 3' (SEQ ID NO: 32) |
| | | pCold-ZZ-P-V44I-KAZ | c | KAZ: A54I-F | 5' AAT GGG TTA AAA ATC GAT ATT CAT GTC 3' (SEQ ID NO: 33) |
| | | | d | KAZ-5C/XbaI | 5' ccgc TCT AGA TTA GGC AAG AAT GTT CTC GCAAAG CCT 3' (SEQ ID NO: 20) |
| | 2nd PCR | 1st PCR product | a | KAZ-8N/EcoRI | 5' gcg AAA TTC TTT ACG TTG GCA GAT TTC GTT GGA 3' (SEQ ID NO: 21) |
| | | | d | KAZ-5C/XbaI | 5' ccgc TCT AGA TTA GGC AAG AAT GTT CTC GCA AAG CCT 3' (SEQ ID NO: 20) |
| V44I-Y138I | 1st PCR | pCold-ZZ-P-Y138I-KAZ | a | KAZ-8N/EcoRI | 5' gcg AAA TTC TTT ACG TTG GCA GAT TTC GTT GGA 3' (SEQ ID NO: 21) |
| | | | b | KAZ: V44I-R | 5' CCC AGA CAG TAC TAT TTT CTG TAT GGG 3' (SEQ ID NO: 30) |
| | | pCold-ZZ-P-Y138I-KAZ | c | KAZ: V44I-F | 5' CCC ATA CAG AAA ATA GTA CTG TCT GGG 3' (SEQ ID NO: 31) |
| | | | d | KAZ-5C/XbaI | 5' ccgc TCT AGA TTA GGC AAG AAT GTT CTC GCA AAG CCT 3' (SEQ ID NO: 20) |
| | 2nd PCR | 1st PCR product | a | KAZ-8N/EcoRI | 5' gcg AAA TTC TTT ACG TTG GCA GAT TTC GTT GGA 3' (SEQ ID NO: 21) |
| | | | d | KAZ-5C/XbaI | 5' ccgc TCT AGA TTA GGC AAG AAT GTT CTC GCAAAG CCT 3' (SEQ ID NO: 20) |
| A54I-Y138I | 1st PCR | pCold-ZZ-P-Y138I-KAZ | a | KAZ-8N/EcoRI | 5' gcg AAA TTC TTT ACG TTG GCA GAT TTC GTT GGA 3' (SEQ ID NO: 21) |
| | | | b | KAZ: A54I-R | 5' GAC ATG AAT ATC GAT TTT TAA CCC ATT 3' (SEQ ID NO: 32) |
| | | pCold-ZZ-P-Y138I-KAZ | c | KAZ: A54I-F | 5' AAT GGG TTA AAA ATC GAT ATT CAT GTC 3' (SEQ ID NO: 33) |
| | | | d | KAZ-5C/XbaI | 5' ccgc TCT AGA TTA GGC AAG AAT GTT CTC GCAAAG CCT 3' (SEQ ID NO: 20) |
| | 2nd PCR | 1st PCR product | a | KAZ-8N/EcoRI | 5' gcg AAA TTC TTT ACG TTG GCA GAT TTC GTT GGA 3' (SEQ ID NO: 21) |
| | | | d | KAZ-5C/XbaI | 5' ccgc TCT AGA TTA GGC AAG AAT GTT CTC GCAAAG CCT 3' (SEQ ID NO: 20) |
| V44I-A54I-Y138I | 1st PCR | pCold-ZZ-P-V44I-Y138I-KAZ | a | KAZ-8N/EcoRI | 5' gcg AAA TTC TTT ACG TTG GCA GAT TTC GTT GGA 3' (SEQ ID NO: 21) |
| | | | b | KAZ: A54I-R | 5' GAC ATG AAT ATC GAT TTT TAA CCC ATT 3' (SEQ ID NO: 32) |

TABLE 6-continued

List of templates and PCR primers
used for KAZ proteins with two and three amino acid substitutions

| Substitution position | Template | | Primer | Sequence |
|---|---|---|---|---|
| | pCold-ZZ-P-V44I-Y138I-KAZ | c | KAZ: A54I-F | 5' AAT GGG TTA AAA ATC GAT ATT CAT GTC 3' (SEQ ID NO: 33) |
| | | d | KAZ-5C/XbaI | 5' ccgc TCT AGA TTA GGC AAG AAT GTT CTC GCA AAG CCT 3' (SEQ ID NO: 20) |
| 2nd PCR | 1st PCR product | a | KAZ-8N/EcoRI | 5' gcg GAA TTC TTT ACG TTG GCA GAT TTC GTT GGA 3' (SEQ ID NO: 21) |
| | | d | KAZ-5C/XbaI | 5' ccgc TCT AGA TTA GGC AAG AAT GTT CTC GCA AAG CCT 3' (SEQ ID NO: 20) |

Example 13

Construction of Expression Vectors for KAZ Mutants with Two Amino Acid Substitutions and Three Amino Acid Substitutions Using pCold II Vector E. coli The DNA fragment obtained in EXAMPLE 12 was purified with a PCR purification kit (manufactured by QIAGEN Inc.), digested with restriction enzymes EcoRI/XbaI and then ligated to the restriction enzyme EcoRI/XbaI site of the expression vector pCold II (Takara Bio Inc.) to construct the expression vectors of pCold-KAZ-V44I-A54I, pCold-ZZ-V44I-Y138I, pCold-KAZ-A54I-Y138I and pCold-KAZ-V44I-A54I-Y138I for the KAZ mutants. The nucleotide sequences of the insert DNAs were confirmed by sequencing using a DNA Sequencer (manufactured by ABI Inc.).

In the amino acid sequences of the KAZ mutants, the substituted amino acids and nucleotides are shown in TABLE 7.

TABLE 7

Substituted amino acids and nucleotides of KAZ mutants

| KAZ Mutants (KAZ-) | Nucleotide Sequence | |
|---|---|---|
| | Before Substitution (wild) | After Substitution (mutant) |
| V44I-A54I | 130 GTT (V), 160 GCT (A) | 130 ATC (I), 160 ATC (I) |
| V44I-Y138I | 130 GTT (V), 412 TAT (Y) | 130 ATC (I), 412 ATC (I) |
| A54I-Y138I | 160 GCT (A), 412 TAT (Y) | 160 ATC (I), 412 ATC (I) |
| V44I-A54I-Y138I | 130 GTT (V), 160 GCT (A), 412 TAT (Y) | 130 ATC (I), 160 ATC (I), 412 ATC (I) |

Herein, the nucleotide sequence and amino acid sequence of KAZ-V44I-A54I are shown by SEQ ID NO: 9 and SEQ ID NO: 10, respectively. The nucleotide sequence and amino acid sequence of KAZ-V44I-Y138I are shown by SEQ ID NO: 11 and SEQ ID NO: 12, respectively. The nucleotide sequence and amino acid sequence of KAZ-A54I-Y138I are shown by SEQ ID NO: 13 and SEQ ID NO: 14, respectively. The nucleotide sequence and amino acid sequence of KAZ-V44I-A54I-Y138I are shown by SEQ ID NO: 15 and SEQ ID NO: 16, respectively.

Example 14

Expression of KAZ Mutants in E. coli and Preparation of Crude Enzyme Solutions

Figure 3:
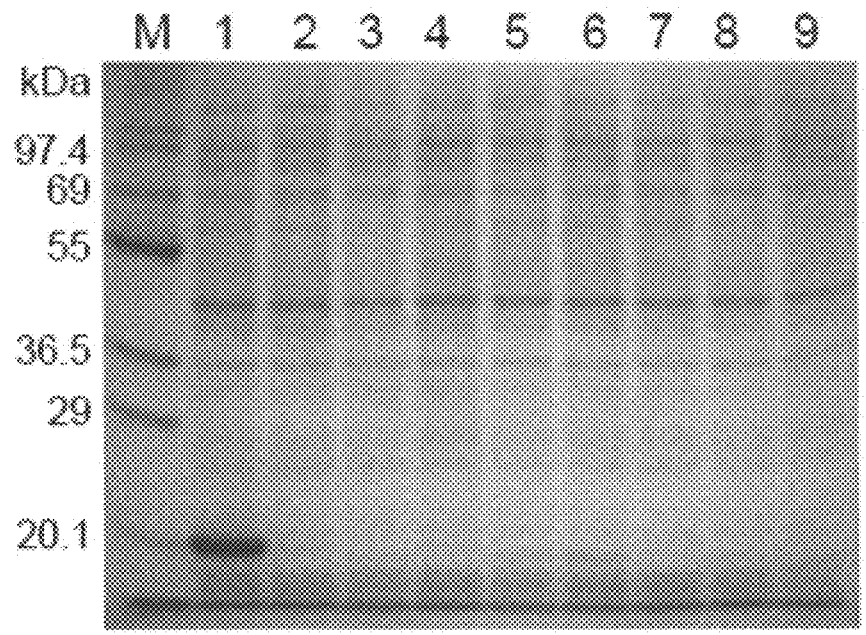
FIG. 3 shows the results of SDS-PAGE analysis of the supernatant and precipitate fractions from the crude enzyme solution of *E. coli* in which the KAZ mutants were expressed using pCold II vector.
Figure 3:
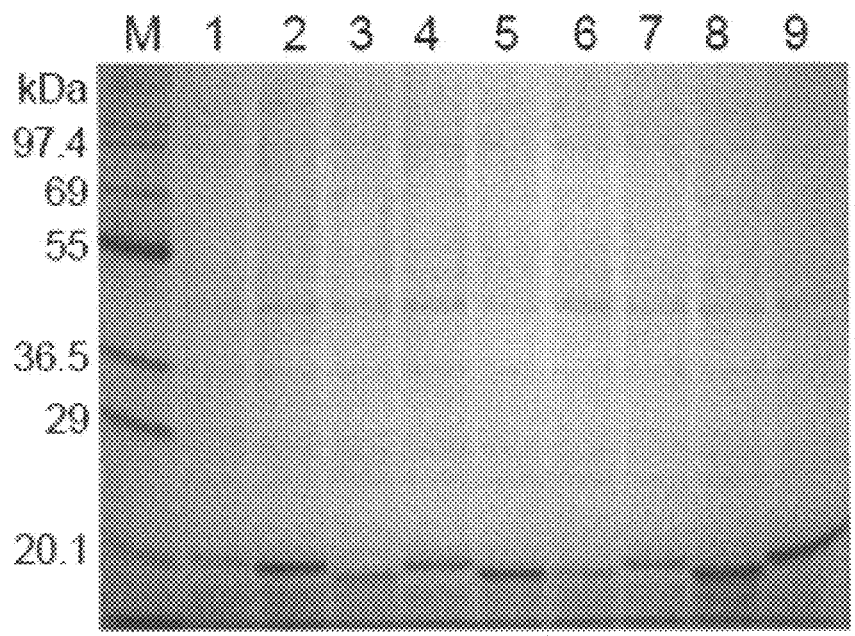

To express the KAZ mutants with two amino acid substitutions and three amino acid substitutions in E. coli using a pCold II vector, the recombinant plasmid constructed in EXAMPLE 13 and pCold-V44I-KAZ, pCold-A54I-KAZ, pCold-Y138I-KAZ prepared in EXAMPLE 3 were used. The supernatant and precipitate of each crude enzyme solution were prepared in the same manner as EXAMPLE 4, using the E. coli BL21 starin (Novagen, Madison, Wis.) as a host cell. The supernatant and precipitate, 20 μL each, were subjected to SDS-PAGE analysis to confirm the presence or absence of soluble proteins and insoluble proteins. The results are shown in FIG. 3. In FIG. 3, M and 1 to 9 are as follows. M: molecular weight markers; 1: dnKAZ; 2: KAZ; 3: KAZ-V44I-A54I; 4: KAZ-V44I-Y138I; 5: KAZ-A54I-Y138I; 6: KAZ-V44I-A54I-Y138I; 7: KAZ-V44I; 8: KAZ-A54I; and 9: KAZ-Y138I. The results of FIG. 3 reveal that only dnKAZ was expressed as a soluble protein and the other mutants and KAZ were expressed as insoluble proteins.

Example 15

Determination of Luminescence Activity of KAZ Mutants in Crude Enzyme Solutions

The luminescence activities of 5 μL each of the supernatant and precipitate obtained in EXAMPLE 14 were determined in the same manner as EXAMPLE 5. The luminescence activity was assayed with a luminometer (manufactured by Atto Inc.: AB2200) for 60 seconds, and the maximum intensity of luminescence ($I_{max}$) was shown as relative luminescence activity.

The results are shown in TABLE 8. As shown in TABLE 8, nevertheless the KAZ mutants were expressed as insoluble proteins, the KAZ mutants with two amino acid substitutions of KAZ-V44I-A54I, KAZ-V44I-Y138I and KAZ-A54I-Y138I in the supernatants showed 295-fold, 71-fold and 982-fold higher activities, respectively, as compared to the wild KAZ. In particular, the KAZ mutants with three amino acid substitutions showed high luminescence activities comparable to dnKAZ, suggesting that these three amino acids may be associated with luminescence enhancement of KAZ.

TABLE 8

Luminescence activities of the supernatant and precipitate fractions in crude enzyme solutions of the mutants

| Expression Vector (pCold-) | Relative Luminescence Activity ($I_{max}$) | |
|---|---|---|
| | Supernatant | Precipitate |
| KAZ | 1.0 | 0.1 |
| KAZ-V44I | 6.5 | 0.6 |
| KAZ-A54I | 151 | 13 |
| KAZ-Y138I | 32 | 1.4 |
| KAZ-V44I-A54I | 295 | 5.8 |
| KAZ-V44I-Y138I | 71 | 5.0 |
| KAZ-A54I-Y138I | 982 | 21 |
| KAZ-V44I-A54I-Y138I | 1,730 | 40 |
| dnKAZ | 1,809 | 10 |

Example 16

Construction of ZZ-Fused KAZ Mutants with Two Amino Acid Substitutions and Three Amino Acid Substitutions in E. coli To express as a soluble protein, the DNA fragment obtained in EXAMPLE 12 was fused to the ZZ domain. The pCold-ZZ-P vector was used in the same manner as EXAMPLE 6 to construct four expression vectors for expressing the KAZ mutants fused to the ZZ domain: pCold-ZZ-P-KAZ-V44I-A54I, pCold-ZZ-P-KAZ-V44I-Y138I, pCold-ZZ-P-KAZ-A54I-Y138I and pCold-ZZ-P-KAZ-V44I-A54I-Y138I.

Example 17

Figure 4:
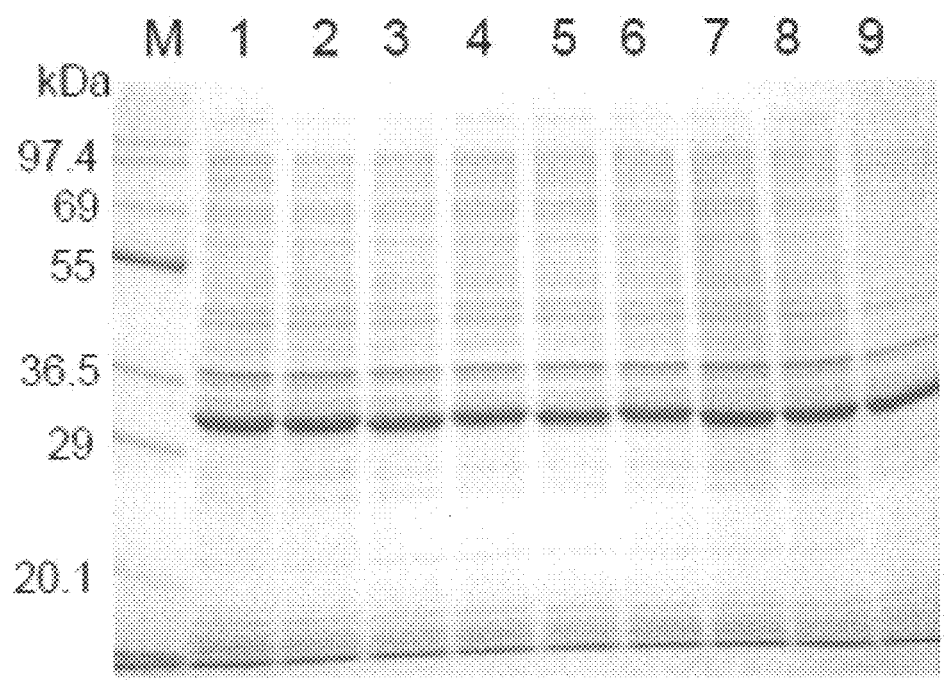
FIG. 4 shows the results of SDS-PAGE analysis of the crude enzyme solution of *E. coli* in which the KAZ mutants were expressed using pCold-ZZ-P vector.

Expression of KAZ Mutants with Two Amino Acid Substitutions and Three Amino Acid Substitutions in E. coli and Preparation of Crude Enzyme Solutions To express the ZZ-fused KAZ mutants in E. coli, the recombinant plasmid constructed in EXAMPLE 16 and pCold-ZZ-P-V44I-KAZ, pCold-ZZ-P-A54I-KAZ, pCold-ZZ-P-Y138I-KAZ prepared in EXAMPLE 6 were used. Crude enzyme solutions were prepared in the same manner as EXAMPLE 7, using the E. coli BL21 strain (Novagen, Madison, Wis.) as a host cell. DTT was added to the crude enzyme solutions at a final concentration of 1 mM. The mixtures were allowed to stand over 5 hours on ice, and luminescence activities were then assayed. The luminescence activities were determined by the method described in EXAMPLE 8. Also, 5 μL of the resultant crude enzyme solutions were subjected to SDS-PAGE analysis to confirm protein expression (FIG. 4). In FIG. 4, M and 1 to 9 are as follows. M: molecular weight size markers; 1: ZZ-P-KAZ; 2: ZZ-P-KAZ-V44I; 3: ZZ-P-KAZ-A54I; 4: ZZ-P-KAZ-Y138I; 5: ZZ-P-KAZ-V44I-A54I; 6: ZZ-P-KAZ-V44I-Y138I; 7: ZZ-P-KAZ-A54I-Y138I; 8: ZZ-P-KAZ-V44I-A54I-Y138I; and 9: ZZ-P-dnKAZ.

TABLE 9

Luminescence activities of ZZ-fused KAZ mutants in crude enzyme solutions

| Expression Vector (pCold-ZZ-P-) | Relative Luminescence Activity ($I_{max}$) |
|---|---|
| KAZ | 1.0 |
| KAZ-V44I | 7.2 |
| KAZ-A54I | 8.4 |
| KAZ-Y138I | 7.5 |
| KAZ-V44I-A54I | 15.3 |
| KAZ-V44I-Y138I | 17.1 |
| KAZ-A54I-Y138I | 23.1 |
| KAZ-V44I-A54I-Y138I | 66.7 |
| dnKAZ | 9.4 |

The results of TABLE 9 reveal that the three mutants of KAZ-V44I-A54I, KAZ-V44I-Y138I and KAZ-A54I-Y138I with two amino acid substitutions showed 15-fold, 17-fold and 23-fold higher activity, respectively, and the mutant KAZ-V44I-A54I-Y138I with three amino acid substitutions showed 67-fold higher activity, than wild KAZ.

In contrast to the relative activity of 9.4 for dnKAZ, the mutants with two amino acid substitutions of KAZ-V44I-A54I, KAZ-V44I-Y138I and KAZ-A54I-Y138I showed 1.6-fold, 1.8-fold and 2.5-fold higher activities than dnKAZ, having 9.4-fold higher activity than KAZ, respectively, and the mutant KAZ-V44I-A54I-Y138I with three amino acid substitutions showed 7.1-fold higher activity than dnKAZ. The results reveal that these three amino acids are critical for enhancement of the luminescence activities.

Example 18

Substrate Specificities of KAZ Mutants with Two Amino Acid Substitutions and KAZ Mutants with Three Amino Acid Substitutions The coelenterazine analogues used for substrate specificity studies were synthesized by the methods described in publications. Specifically, bis-coelenterazine was synthesized by the method described in Nakamura et al. (1997) Tetrahedron Lett. 38: 6405-6406; furimazine by the method described in Hall et al. (2012) ACS Chem. Biol. 16; 848-1857; and, 6h-coelenterazine, f-coelenterazine and 6h-f-coelenterazine by the methods described in Inouye et al (2013) Biochem. Biophys. Res. Commun. 437: 23-28.

DTT was added to the crude enzyme solutions obtained in EXAMPLE 17 at a final concentration of 1 mM and the mixtures were allowed to stand in an ice water for more than 5 hours in the same manner as Example 8. A luminescence reaction was started by the addition of 1 μL each of the crude enzyme solutions to 100 μL of TE containing 1 μg of coelenterazine (manufactured by JNC Corp.) or its analogues. The luminescence activities were determined using a luminometer (manufactured by Atto Inc.: AB2200) for 60 seconds, and the maximum intensity of luminescence ($I_{max}$) was shown as relative luminescence activity.

The results are shown in TABLE 10. The results of TABLE 10 reveal that, when coelenterazine was used as a substrate, the mutants with two amino acid substitutions and the mutants with three amino acid substitutions showed higher luminescence activities than dnKAZ, in particular, the mutants with three amino acid substitutions showed highest luminescence activities.

The mutant of KAZ-V44I-A54I-Y138I with three amino acid substitutions also showed higher luminescence activity than dnKAZ with 6h-coelenterazine.

It was revealed that the mutants of KAZ-V44I-A54I, KAZ-V44I-Y138I, KAZ-A54I-Y138I and KAZ-V44I-A54I-Y138I show high substrate specificity for coelenterazine.

TABLE 10

Substrate specificities of KAZ mutants

| | Relative Luminescence Activity | | | | | | | | | | | | | |
|---|---|---|---|---|---|---|---|---|---|---|---|---|---|---|
| | CTZ | | h-CTZ | | 6h-CTZ | | bis-CTZ | | f-CTZ | | 6h-f-CTZ | | Furimazine | |
| KAZ Mutant | $I_{max}$ | Int. | $I_{max}$ | Int. | $I_{max}$ | Int. | $I_{max}$ | Int. | $I_{max}$ | Int. | $I_{max}$ | Int. | $I_{max}$ | Int. |
| KAZ | 1.0 | 1.0 | 1.1 | 0.7 | 0.1 | 0.2 | 0.6 | 0.9 | 0.9 | 0.8 | 0.6 | 0.7 | 0.4 | 0.5 |
| V44I | 7.2 | 5.9 | 3.7 | 2.2 | 0.4 | 0.6 | 1.1 | 1.4 | 2.1 | 2.0 | 0.6 | 0.7 | 0.6 | 0.9 |
| A54I | 8.4 | 9.0 | 11.8 | 6.9 | 1.6 | 2.1 | 3.0 | 3.4 | 8.2 | 4.9 | 1.6 | 2.0 | 2.0 | 2.1 |
| Y138I | 7.5 | 5.9 | 3.9 | 3.0 | 0.2 | 0.3 | 1.3 | 1.5 | 2.4 | 2.4 | 0.6 | 0.8 | 0.6 | 0.8 |
| V44I-A54I | 15.3 | 12.7 | 17.9 | 8.7 | 4.5 | 5.6 | 5.7 | 5.9 | 11.3 | 5.2 | 3.2 | 4.0 | 3.4 | 4.3 |
| V44I-Y138I | 17.1 | 9.9 | 19.1 | 9.7 | 4.3 | 5.3 | 7.9 | 8.3 | 13.3 | 7.4 | 3.6 | 4.2 | 5.1 | 5.4 |
| A54I-Y138I | 23.1 | 19.1 | 24.2 | 12.9 | 5.8 | 6.1 | 9.5 | 9.2 | 19.7 | 9.2 | 5.2 | 5.7 | 5.9 | 5.8 |
| V44I-A54I-Y138I | 66.7 | 66.7 | 83.1 | 33.2 | 12.9 | 11.1 | 13.3 | 11.9 | 43.8 | 9.5 | 9.5 | 9.6 | 10.6 | 9.2 |
| dnKAZ (16 mutants) | 9.1 | 7.9 | 161.2 | 109.1 | 6.8 | 4.8 | 112.0 | 90.2 | 146.3 | 75.5 | 111.2 | 68.1 | 65.1 | 66.8 |

$I_{max}$: Maximum intensity of luminescence,
Int.: Relative intensity of luminescence integrated for 60 seconds Example 19

Construction of Secretory Expression Vector for the KAZ Mutants with Two Amino Acid Substitutions and Three Amino Acid Substitutions Using a Signal Peptide Sequence of *Gaussia* Luciferase for Secretion Vectors for the secretory expression of the KAZ mutants with two amino acid substitutions and three amino acid substitutions were constructed using the signal peptide sequence of *Gaussia* luciferase for secretion, as follows. Using the pcDNA3-GLsp-vector prepared in EXAMPLE 8, the gene fragments of the KAZ mutants with two amino acid substitutions and three amino acid substitutions prepared in EXAMPLE 12 and the dnKAZ gene fragment prepared in EXAMPLE 2 were digested with restriction enzymes EcoRI/XbaI in a conventional manner, and ligated to the EcoRI-XbaI site of pcDNA3-GLsp to construct the expression vectors of pcDNA3-GLsp-KAZ-V44I-A54I, pcDNA3-GLsp-KAZ-V44I-Y138I, pcDNA3-GLsp-KAZ-A54I-Y138I, pcDNA3-GLsp-KAZ-V44I-A54I-Y138I and pcDAN3-GLsp-dnKAZ. The sequences of genes inserted were confirmed by sequencing using a DNA Sequencer (manufactured by ABI Inc.).

Example 20

Transfection of Vectors into Animal Culture Cells and Preparation of Enzyme for Assay (1) Purification of Expression Plasmids The recombinant plasmids obtained in EXAMPLE 19 were purified in the same manner as EXAMPLE 10 and dissolved in sterilized water. Firefly luciferase vector (pGL4.13 [Luc2/sv40]: manufactured by Promega Corp.) was similarly treated and used as an internal standard.

(2) Transfection and Preparation of Enzyme Solutions for Assay

Culture media of the KAZ mutants with two amino acid substitutions and KAZ mutants with three amino acid substitutions and the enzyme solutions of the cell-extracts of KAZ mutants were prepared in the same manner as EXAMPLE 10.

In the resultant enzyme solutions and the enzyme solutions of the cell-extracts of KAZ mutants, luminescence activities were determined in the same manner as EXAMPLE 11.

The results are shown in TABLE 11. Based on the results of TABLE 11, the KAZ mutants with two amino acid substitutions and three amino acid substitutions expressed using the signal peptide sequence of *Gaussia* luciferase for secretion were hardly secreted from the cells as compared to dnKAZ, in spite of being expressed in the cytoplasm.

TABLE 11

Luminescence activities of KAZ mutants expressed using vectors for secretory expression of KAZ mutants using the signal peptide sequence of *Gaussia* luciferase for secretion

| Expression Vector | Relative Luminescence Activity (%, $I_{max}$) | |
|---|---|---|
| (pcDNA3-GLsp-) | Culture Medium | Cell Extracts |
| KAZ | less than 0.01 | 0.3 |
| KAZ-V44I-A54I | 0.07 | 13.9 |
| KAZ-V44I-Y138I | less than 0.01 | 11.2 |
| KAZ-A54I-Y138I | 0.03 | 16.0 |
| KAZ-V44I-A54I-Y138I | 1.7 | 16.2 |
| dnKAZ | 100 | 12.6 |

Example 21

Construction of Expression Vectors for KAZ Mutants with Two Amino Acid Substitutions and Three Amino Acid Substitutions without Signal Peptide Sequence for Secretion in Animal Culture Cells The gene fragments of the KAZ mutants with two amino acid substitutions and three amino acid substitutions and nanoKAZ containing the Kozak sequence were digested with restriction enzymes Asp718 and XbaI, and inserted into the Asp718-XbaI site of pcDNA3 vector (manufactured by Invitrogen Inc.) to construct the vectors of pcDNA3-KAZ-V44I, pcDNA3-KAZ-A54I, pcDNA3-KAZ-Y138I, pcDNA3-KAZ-V44I-A54I, pcDNA3-KAZ-V44I-Y138I, pcDNA3-KAZ-A54I-Y138I and pcDNA3-KAZ-V44I-A54I-Y138I.

Example 22

Transfection of Vectors in Animal Culture Cells and Preparation of Enzyme Solution for Assay (1) Purification of Expression Plasmids The recombinant plasmids obtained in EXAMPLE 21 were purified in the same manner as EXAMPLE 10 and dissolved in sterile water. Firefly luciferase vector (pGL4.13 [Luc2/sv40]: manufactured by Promega Corp.) was similarly treated and used as an internal standard.

(2) Transfection and Preparation of Enzyme for Assay

The culture media of the KAZ mutants with two amino acid substitutions and KAZ mutants with three amino acid substitutions and the enzyme solutions of cell-extracts of KAZ mutants were obtained in the same manner as EXAMPLE 10.

Luminescence activities of the resulting enzyme solutions and enzyme solutions of the cell-extracts of KAZ mutants were determined in the same manner as EXAMPLE 11.

The results are shown in TABLE 12. It is understood from TABLE 12 that the KAZ mutants with two amino acid substitutions and three amino acid substitutions, which were expressed using the expression vectors for the KAZ mutants without a secretion signal, showed higher luminescence activities, specifically, KAZ-V44I was 3.7-fold higher, KAZ-A54I 6.7-fold higher, KAZ-Y138I 6.4-fold higher, KAZ-V44I-A54I 23-fold higher, KAZ-V44I-Y138I 15-fold higher, KAZ-A54I-Y138I 22-fold higher and KAZ-V44I-A54I-Y138I 56-fold higher in the cell extracts, than wild KAZ. In particular, the KAZ mutants with two amino acid substitutions and the KAZ mutants with three amino acid substitutions showed higher activities than wild KAZ.

On the other hand, secretion from the cells was hardly observed in all of the mutants, notwithstanding that the luminescence activities were found to be higher in the cytoplasm than wild KAZ.

TABLE 12

Luminescence activities of KAZ mutants using expression vectors for the KAZ mutants without a secretional signal peptide sequence

| Expression Vector (pcDNA3-) | Relative Luminescence Activity ($I_{max}$) | | Rate of Secretion (Medium/Cell Extracts) |
|---|---|---|---|
| | Culture Medium | Cell Extracts | |
| KAZ | 0.03 | 1.0 | 0.03 |
| KAZ-V44I | 0.06 | 3.7 | 0.016 |
| KAZ-A54I | 0.03 | 6.7 | 0.0045 |
| KAZ-Y138I | 0.03 | 6.4 | 0.0047 |
| KAZ-V44I-A54I | 0.05 | 22.5 | 0.0022 |
| KAZ-V44I-Y138I | 0.04 | 14.7 | 0.0026 |
| KAZ-A54I-Y138I | 0.05 | 21.5 | 0.0023 |
| KAZ-V44I-A54I-Y138I | 0.08 | 56.0 | 0.0014 |

These results reveal that the two amino acid substituted KAZ mutants of KAZ-V44I-A54I, KAZ-V44I-Y138I and KAZ-A54I-Y138I and the three amino acid substituted KAZ mutant of KAZ-V44I-A54I-Y138I showed markedly higher luminescence activities than wild KAZ when coelenterazine was used as a substrate, and these mutants have the property that they are not secreted from animal culture cells. The mutants are therefore suitable for a reporter assay in the cytoplasm.

SEQUENCE LISTING FREE TEXT

[SEQ ID NO: 1] Nucleotide sequence for KAZ
[SEQ ID NO: 2] Amino acid sequence for KAZ
[SEQ ID NO: 3] Nucleotide sequence for KAZ-V44I
[SEQ ID NO: 4] Amino acid sequence for KAZ-V44I
[SEQ ID NO: 5] Nucleotide sequence for KAZ-A54I
[SEQ ID NO: 6] Amino acid sequence for KAZ-A54I
[SEQ ID NO: 7] Nucleotide sequence for KAZ-Y138I
[SEQ ID NO: 8] Amino acid sequence for KAZ-Y138I
[SEQ ID NO: 9] Nucleotide sequence for KAZ-V44I-A54I
[SEQ ID NO: 10] Amino acid sequence for KAZ-V44I-A54I
[SEQ ID NO: 11] Nucleotide sequence for KAZ-V44I-Y138I
[SEQ ID NO: 12] Amino acid sequence for KAZ-V44I-Y138I
[SEQ ID NO: 13] Nucleotide sequence for KAZ-A54I-Y138I
[SEQ ID NO: 14] Amino acid sequence for KAZ-A54I-Y138I
[SEQ ID NO: 15] Nucleotide sequence for KAZ-V44I-A54I-Y138I
[SEQ ID NO: 16] Amino acid sequence for KAZ-V44I-A54I-Y138I
[SEQ ID NO: 17] Nucleotide sequence used in EXAMPLES (pCold-F)
[SEQ ID NO: 18] Nucleotide sequence used in EXAMPLES (KAZ: Q18L-R)
[SEQ ID NO: 19] Nucleotide sequence used in EXAMPLES (KAZ: Q18L-F)
[SEQ ID NO: 20] Nucleotide sequence used in EXAMPLES (KAZ-5C/XbaI)
[SEQ ID NO: 21] Nucleotide sequence used in EXAMPLES (KAZ-8N/EcoRI)
[SEQ ID NO: 22] Nucleotide sequence used in EXAMPLES (KAZ: A4E-F)
[SEQ ID NO: 23] Nucleotide sequence used in EXAMPLES (KAZ: Q11R-F)
[SEQ ID NO: 24] Nucleotide sequence used in EXAMPLES (KAZ: L27V-R)
[SEQ ID NO: 25] Nucleotide sequence used in EXAMPLES (KAZ: L27V-F)
[SEQ ID NO: 26] Nucleotide sequence used in EXAMPLES (A33N-R)
[SEQ ID NO: 27] Nucleotide sequence used in EXAMPLES (A33N-F)
[SEQ ID NO: 28] Nucleotide sequence used in EXAMPLES (KAZ: K43R-R)
[SEQ ID NO: 29] Nucleotide sequence used in EXAMPLES (KAZ: L43R-F)
[SEQ ID NO: 30] Nucleotide sequence used in EXAMPLES (KAZ: V44I-R)
[SEQ ID NO: 31] Nucleotide sequence used in EXAMPLES (KAZ: V44I-F)
[SEQ ID NO: 32] Nucleotide sequence used in EXAMPLES (KAZ: A54I-R)
[SEQ ID NO: 33] Nucleotide sequence used in EXAMPLES (KAZ: A54I-F)
[SEQ ID NO: 34] Nucleotide sequence used in EXAMPLES (pCold-R)
[SEQ ID NO: 35] Nucleotide sequence used in EXAMPLES (KAZ: F68D-R)

[SEQ ID NO: 36] Nucleotide sequence used in EXAMPLES (KAZ: F68D-F)
[SEQ ID NO: 37] Nucleotide sequence used in EXAMPLES (KAZ: L72Q-R)
[SEQ ID NO: 38] Nucleotide sequence used in EXAMPLES (KAZ: L72Q-F)
[SEQ ID NO: 39] Nucleotide sequence used in EXAMPLES (KAZ: M75K-R)
[SEQ ID NO: 40] Nucleotide sequence used in EXAMPLES (KAZ: M75K-F)
[SEQ ID NO: 41] Nucleotide sequence used in EXAMPLES (KAZ: I90V-R)
[SEQ ID NO: 42] Nucleotide sequence used in EXAMPLES (KAZ: I90V-F)
[SEQ ID NO: 43] Nucleotide sequence used in EXAMPLES (KAZ: P115E-R)
[SEQ ID NO: 44] Nucleotide sequence used in EXAMPLES (KAZ: P115E-F)
[SEQ ID NO: 45] Nucleotide sequence used in EXAMPLES (KAZ: Q124K-R)
[SEQ ID NO: 46] Nucleotide sequence used in EXAMPLES (KAZ: Q124K-F)
[SEQ ID NO: 47] Nucleotide sequence used in EXAMPLES (KAZ: Y138I-R)
[SEQ ID NO: 48] Nucleotide sequence used in EXAMPLES (KAZ: Y138I-F)
[SEQ ID NO: 49] Nucleotide sequence used in EXAMPLES (KAZ: N166R-R)
[SEQ ID NO: 50] Nucleotide sequence used in EXAMPLES (nanoKAZ-1N/EcoRI)
[SEQ ID NO: 51] Nucleotide sequence used in EXAMPLES (nanoKAZ-3C/XbaI)
[SEQ ID NO: 52] Nucleotide sequence used in EXAMPLES (GLsp-1R/EcoRI)
[SEQ ID NO: 53] Nucleotide sequence used in EXAMPLES (T7 primer)

The invention claimed is:

1. A luciferase mutant defined in (a) or (b) below:
    (a) a luciferase mutant comprising the amino acid sequence of SEQ ID NO: 2 substituted at the positions consisting of the valine at position of 44, the alanine at position 54, and the tyrosine at position 138, wherein the luciferase mutant has luciferase activity; and
    (b) a luciferase mutant comprising the amino acid sequence of SEQ ID NO: 2 substituted at the positions consisting of:
        (1) the valine at position of 44, the alanine at position 54, and the tyrosine at position 138; and
        (2) one to sixteen positions, none of which includes any one of the positions 4, 11, 18, 27, 33, 43, 68, 72, 75, 90, 115, 124, and 166, wherein the luciferase mutant has luciferase activity.

2. The luciferase mutant according to claim 1, wherein the luciferase mutant comprises the amino acid sequence of SEQ ID NO: 2 substituted at the positions consisting of:
    (1) the valine at position of 44, the alanine at position 54, and the tyrosine at position 138; and
    (2) one to ten positions, none of which includes any one of the positions 4, 11, 18, 27, 33, 43, 68, 72, 75, 90, 115, 124, and 166.

3. The luciferase mutant according to claim 1, wherein the valine at position 44 is substituted by an isoleucine, the alanine at position 54 is substituted by an isoleucine, and the tyrosine at position 138 is substituted by an isoleucine.

4. The luciferase mutant according to claim 1, comprising the amino acid sequence of SEQ ID NO: 16.

5. A kit comprising the luciferase mutant according to claim 1.

6. The kit according to claim 5, further comprising a luciferin.

7. The kit according to claim 6, wherein the luciferin is coelenterazines.

8. The kit according to claim 7, wherein the coelenterazines is coelenterazine.

* * * * *